US012735520B2

(12) United States Patent
Meier et al.

(10) Patent No.: US 12,735,520 B2
(45) Date of Patent: Sep. 15, 2026

(54) THIOL URETHANE GROUP-CONTAINING POLYMERIZABLE COMPOSITION

(71) Applicant: Kulzer GmbH, Hanau (DE)

(72) Inventors: Christoph Meier, Bruchkoebel (DE); Andreas Utterodt, Neu-Anspach (DE); Kurt Reischl, Merenberg (DE); Jutta Schneider, Runkel (DE); Michael Eck, Schmitten (DE); Raif Kocoglu, Woelfersheim (DE); Nelli Schoenhof, Braunfels (DE)

(73) Assignee: Kulzer GmbH, Hanau (DE)

( * ) Notice: Subject to any disclaimer, the term of this patent is extended or adjusted under 35 U.S.C. 154(b) by 196 days.

(21) Appl. No.: 18/564,497

(22) PCT Filed: May 25, 2022

(86) PCT No.: PCT/EP2022/064194

§ 371 (c)(1),
(2) Date: Nov. 27, 2023

(87) PCT Pub. No.: WO2022/248546

PCT Pub. Date: Dec. 1, 2022

(65) Prior Publication Data

US 2025/0092176 A1 Mar. 20, 2025

(30) Foreign Application Priority Data

May 27, 2021 (DE) .................... 10 2021 113 777.2

(51) Int. Cl.

| | |
|---|---|
| ***C09J 11/04*** | (2006.01) |
| ***A61K 6/17*** | (2020.01) |
| ***A61K 6/71*** | (2020.01) |
| ***C08F 222/10*** | (2006.01) |
| ***C08F 290/14*** | (2006.01) |
| ***C08G 18/38*** | (2006.01) |
| ***C08G 18/76*** | (2006.01) |
| ***C08G 18/80*** | (2006.01) |
| ***C08K 3/013*** | (2018.01) |
| ***C08K 3/16*** | (2006.01) |
| ***C08K 9/06*** | (2006.01) |
| ***C09J 123/00*** | (2006.01) |
| ***C09J 175/04*** | (2006.01) |
| ***C09J 181/04*** | (2006.01) |
| ***E06B 3/673*** | (2006.01) |

(52) U.S. Cl.

CPC .......... *C08F 222/1025* (2020.02); *A61K 6/17* (2020.01); *A61K 6/71* (2020.01); *C08F 290/147* (2013.01); *C08G 18/3876* (2013.01); *C08G 18/7642* (2013.01); *C08G 18/8064* (2013.01); *C08K 3/013* (2018.01); *C08K 3/16* (2013.01); *C08K 9/06* (2013.01)

(58) Field of Classification Search

CPC ....... C08F 222/1025; A61K 6/17; A61K 6/71; C08G 18/3876; C08G 18/7642; C08K 3/013; C08K 3/16; C08K 9/06

USPC .......................................................... 428/220

See application file for complete search history.

(56) References Cited

U.S. PATENT DOCUMENTS

| | | | | |
|---|---|---|---|---|
| 8,003,748 | B2 * | 8/2011 | Byers ................ | C08G 18/3876 528/84 |
| 9,795,541 | B2 | 10/2017 | Fontein et al. | |
| 10,130,564 | B2 | 11/2018 | Yoshinaga et al. | |
| 10,857,073 | B2 | 12/2020 | Moszner et al. | |
| 11,701,304 | B2 | 7/2023 | Suzuki et al. | |
| 2007/0185230 | A1 | 8/2007 | Bowman et al. | |
| 2011/0144227 | A1 * | 6/2011 | Bowman ............. | C08G 18/673 522/96 |
| 2016/0128909 | A1 * | 5/2016 | Fontein ................. | A61K 6/887 523/116 |
| 2017/0007505 | A1 | 1/2017 | Moszner et al. | |
| 2021/0179745 | A1 | 6/2021 | Kakinuma | |
| 2021/0246239 | A1 | 8/2021 | Kakinuma et al. | |
| 2022/0153894 | A1 | 5/2022 | Sakamaki et al. | |
| 2022/0195263 | A1 * | 6/2022 | Karrer ................... | C08G 18/69 |

(Continued)

FOREIGN PATENT DOCUMENTS

| | | | | |
|---|---|---|---|---|
| DE | 102019129551 A1 * | 5/2021 | ............ | C08K 3/013 |
| EP | 0 934 926 A1 | 8/1999 | | |
| EP | 3 020 361 A1 | 5/2016 | | |

(Continued)

*Primary Examiner* — Tahseen Khan

(74) *Attorney, Agent, or Firm* — Norris McLaughlin, P.A.

(57) ABSTRACT

An object of the invention is a polymerizable composition comprising.

0.01 to 90 wt.-% of at least one inorganic filler component, 5 to 99.97 wt.-% comprising at least two urethane acrylates, wherein one urethane acrylate corresponding to formula I and the second urethane acrylate having at least one bifunctional thiolurethane group and at least one olefinic group, and mixtures of urethane acrylates comprising these, 0.01 to 25 wt.-% of at least one di-, tri-, tetra- or multi-functional monomer having at least one ether group, thioether group, an at least tri-functional triester and/or a di-functional diester, the diester being selected from tricyclodecanedimethanol dimethacrylate and tricyclodecanedimethanol diacrylate or mixtures of these di-, tri-, tetra- or multi-functional monomers, 0.01 to 10 wt.-% of at least one initiator, an initiator system, and optionally at least one stabilizer and optionally at least one pigment, wherein the total composition of the polymerizable composition is 100 wt.-%.

16 Claims, No Drawings

(56) References Cited

U.S. PATENT DOCUMENTS

2024/0352274 A2* 10/2024 Utterodt .................... C08F 2/48

FOREIGN PATENT DOCUMENTS

| | | | |
|---|---|---|---|
| EP | 3 135 271 | B1 | 5/2019 |
| EP | 3 719 048 | A1 | 10/2020 |
| EP | 3 733 150 | A1 | 11/2020 |
| EP | 3 795 597 | A1 | 3/2021 |
| WO | 2019/107323 | A1 | 6/2019 |
| WO | 2020/203981 | A1 | 10/2020 |

* cited by examiner

THIOL URETHANE GROUP-CONTAINING POLYMERIZABLE COMPOSITION

This application is a 371 of International Patent Application No. PCT/EP2022/064194, filed May 25, 2022, which claims priority of German Patent Application No. 10 2021 113 777.2, filed May 27, 2021, the disclosures of which patent applications are hereby incorporated herein by reference.

An object of the invention is a polymerizable composition comprising 0.01 to 90 wt.-% of at least one inorganic filler component, 5 to 99.97 wt.-% comprising at least two urethane acrylates, at least one urethane acrylate corresponding to formula I and the second urethane acrylate having at least one bifunctional thiolurethane group and at least one olefinic group, and mixtures of urethane acrylates comprising these, 0.01 to 25 wt.-% of at least one di-, tri-, tetra- or multi-functional monomer with at least one ether group, thioether group, an at least tri-functional triester, in particular having thioether group(s), and/or a di-functional diester, the diester being selected from tricyclodecane dimethanol dimethacrylate and tricyclodecane dimethanol diacrylate or mixtures of these di-, tri-, tetra- or multi-functional monomers, 0.01 to 10 wt.-% of at least one initiator, an initiator system and optionally at least one stabilizer and optionally at least one pigment, wherein the total composition of the polymerizable composition is 100 wt.-%. Also, an object of the invention is a polymerized composition having high flexural strength, high transparency and high double bond turnover and optionally low shrinkage in the production of three-dimensional articles or objects greater than 5 mm in at least one of the three dimensions. Likewise, the polymerized compositions exhibit low brittleness.

A combination of bisphenol A glycidyl methacrylate (BisGMA) and triethylene glycol dimethacrylate (TEGDMA) as monomers for dental composites has established itself as one of the standards for dental composites in recent years. Due to the partly proven toxicity of the monomers, they should be substituted by non-toxic monomers with comparable physical properties, which is made possible by the monomer combinations used in this document.

Urethane acrylates with bivalent aromatic groups are known from EP3135271B1. Polymerized compositions based on these urethanes exhibit good flexural strengths and low shrinkage. The urethanes with aromatic groups tend to have increased crystallization compared to other urethanes.

WO2019/107323A1 discloses the preparation of thiols containing (meth)acrylate groups, such as thiocarbamates with at least one (meth)acrylate group. Compositions based on these thiocarbamates exhibit improved fracture strengths. In EP3795597A1,(meth)acrylate-functional thioethers with good fracture strengths and toughness are disclosed. The thioethers have lower viscosities than the thiocarbar bamates of WO2019/107323 A1.

US2017/0007505A1 discloses functional diphenylsufide monomers and U.S. Pat. No. 10,857,073B2 discloses difunctional phenylsufide monomers with high refractive index.

EP3733150A1 discloses polyurethane resins in dental applications from polythiols and polyisocyanates. US2007/0185230 A1 oligomeric thio-ene systems from light-induced conversion of trithio/trivinyl, which are reported to exhibit increased double bond conversion in dental compositions than dimethyl acrylate systems, which exhibit a double bond conversion of 55 to 75% and excessive shrinkage.

To date, there have been only a few publications of these so-called thiol-ene monomers in dental composites. Accordingly, the thiol-ene monomers represent a monomer blend of thiol and acrylate, methacrylate or vinylic monomers. A disadvantage is the odor of these thiol-containing composites. Also, the underlying polymerization mechanism in these monomer blends comprising thiol monomers and acrylate, methacrylate or vinylic monomers is significantly different from the radical polymerization mechanism present in the compositions according to the invention due to a radical chain transfer between thiol and (meth)acrylate. The technologies thus describe fundamentally different technologies.

It was a problem of the invention to further improve the good mechanical properties of urethane acrylates. On the one hand, this was to be done by improving the storage stability of urethanes that tend to crystallize and, alternatively or additionally, by improving the transparency of the polymerized compositions. In addition, the task was to increase the double bond conversion in polymerizable compositions, preferably without negatively affecting the shrinkage of the composition. Furthermore, the mechanical properties of the polymerized compositions should be advantageously improved. Furthermore, an improvement of the E-modulus, especially in combination with an improved depth of cure, should be possible.

The composition according to the invention is described in the independent claims 1 and 12 and in use claims 14 and 15. A more detailed disclosure of the invention is described in the subclaims and in the description.

An object of the invention is a polymerizable composition, in particular a dental composition, preferably a dental composite, comprising polymerizable urethane (alkyl) acrylates, in particular urethane(meth)acrylates, of formula I as well as isomers thereof and urethane(meth)acrylates comprising thiol(meth)acrylates, hereinafter referred to as urethane acrylates with thiol group and olefinic group, which are used as crosslinkers. Furthermore, the polymerizable composition comprises monomers referred to as diluents. These monomers may include di- to multi-functional monomers with ether, thioether groups, triesters or diesters of tricyclodecane monomers. These monomers used as diluents are (meth)acrylate functional monomers.

Surprisingly, it was found that compositions comprising as a urethane acrylate a monomer 1, of formula I,

1

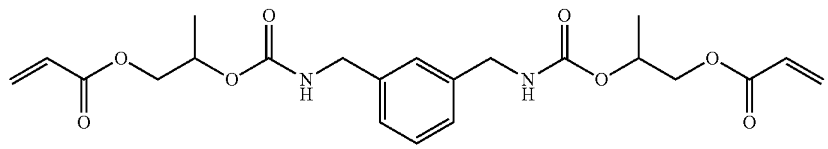

and at least one further urethane acrylate designated as monomer 2, in particular of the formulas V and VI with a thiolurethane group 2a have very good curing depths, flexural strength, E-modulus and improved transparency and increased double bond conversion.

2a (V)

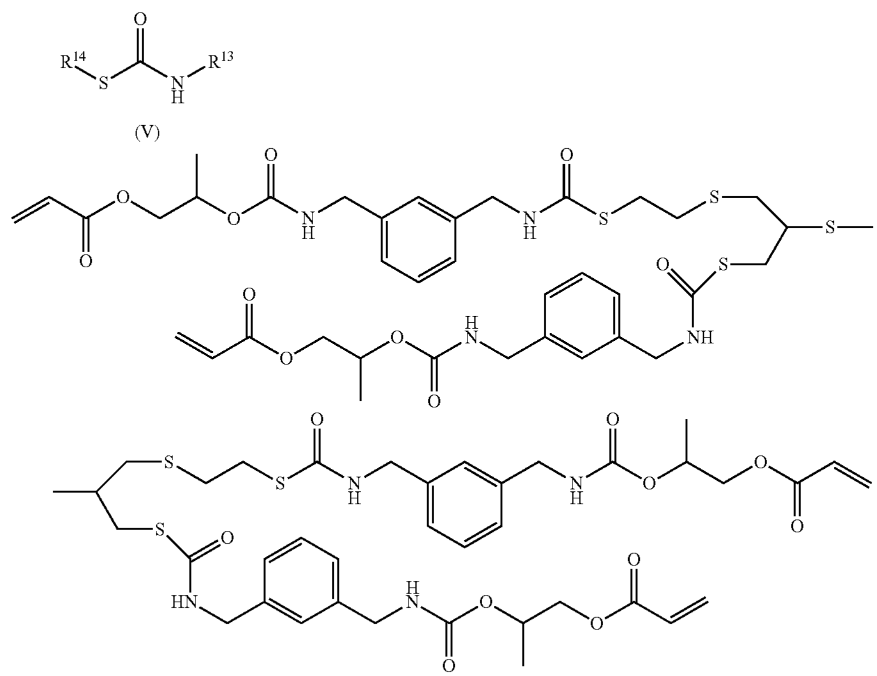

Monomer 2 of the formula V

Formula V with $R^{14}$ equals formula VId with $R^7$ in which $R^8$ is $—CH_2$-Phenyl-$CH_2—$, and $R^{10}$ equals $—CH(CH_3)CH_2—$, and with $R^{15}$ equals H. Monomer 2 with formula VId with $R^7$ in which $R^8$ is $—CH_2$-Phenyl-$CH_2—$, and $R^{10}$ is $—CH(CH_3)CH_2—$, and with $R^{15}$ is H.

And also in composites, the urethane(meth)acrylate of formula I, and particularly preferably monomer 1, shows very good properties in terms of flexural strength, modulus of elasticity (E-modulus) and transparency.

The monomers of formula I can be prepared from corresponding diisocyanates with corresponding hydroxy-functional(meth)acylates or also diols with corresponding isocyanates; the preparation of monomer 1 is disclosed in EP 3135271 B1.

The monomer 1, however, shows an increased tendency to crystallize. Surprisingly, this could be avoided by addition, in particular lower than stoichiometric addition, of a thiol of formula V or VI. The preparation of the thiols is disclosed in WO2019/107323 A1. After addition of the thiol to the corresponding isocyanate, a thiol urethane(meth)acrylate is formed, i.e. thiol ester, with the following general structural formula V, which can be used as monomer 2a or 2 in component (ii) in the composition. Depending on the thiol used, $R^{14}$ according to WO2019/107323 A1 can form different structures.

An object of the invention is a polymerizable composition comprising.

(i) 0.01 to 90 wt.-% of at least one inorganic filler component, (ii) 5 to 99.97 wt.-% comprising at least two urethane acrylates, in particular urethane methacrylates and/or urethane acrylates, wherein one urethane acrylate is at least one urethane acrylate of the formula I having a divalent hydrocarbon group (I)

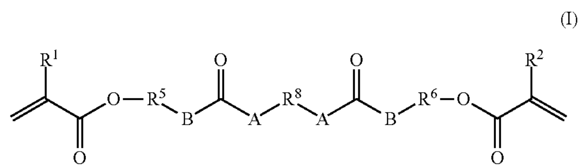

with A=O when B═NH or A=NH when B═O, in particular the above compounds have $R^1$ and $R^2$ each independently selected from H and alkyl having 1 to 8 C-atoms, preferably $R^1$═H or $CH_3$, $R^2$═H or $CH_3$, $R^5$ and $R^6$ each independently selected from linear C2 to C6 alkylene groups or linear C2 to C6 oxyalkylene groups, wherein $R^5$ and $R^6$ optionally each independently have a C1-C3 alkyl group or (meth)acryloxymethylene group, preferably $CH_3$ and $R^8$ is a divalent hydrocarbon group having 6 to 12 carbon atoms, and/or the second urethane acrylate has at least one bifunctional thiolurethane group and at least one olefinic group, and optionally mixtures of urethane acrylates comprising these, in particular urethane acrylates of the formula I and thiourethane(s) of the formula V and/or VI and optionally isomers thereof, (iii) 0.01 to 25 wt.-% of at least one di-, tri-, tetra- or multi-functional monomer having at least one ether group, thioether group, at least one tri-functional triester and/or di-functional diester, said diester being selected from tricyclodecanedimethanol dimethacrylate and tricyclodecanedimethanol diacrylate or mixtures comprising at least two of said di-, tri-, tetra- or multi-functional monomers, (iv) 0.01 to 10 wt.-% of at least one initiator, an initiator system, and optionally at least one stabilizer and optionally at least one pigment and optionally further additives, wherein the total composition of the polymerizable composition is 100 wt.-%.

Preferred urethane acrylates of formula I comprise urethane acrylates of formula Ia (Ia)

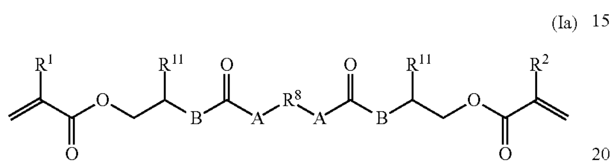

with A=O when B═NH or A=NH when B═O and with $R^1$═H or $CH_3$, $R^2$═H or $CH_3$, and $R^8$ a divalent hydrocarbon group with 6 to 12 C-atoms, $R^{11}$=each independently H, C1-C3 alkyl groups or (meth)acryloxymethylene group, preferably $CH_3$. Preferably, $R^8$ comprises one of the following divalent groups.

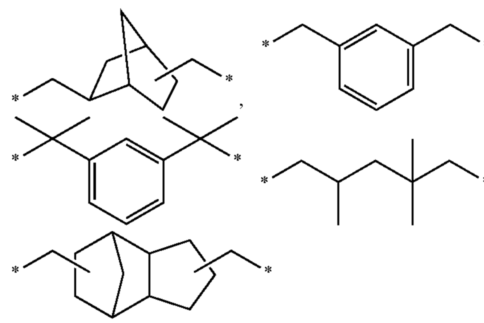

The following specific urethane acrylate, in particular comprising urethane methacrylates and urethane acrylates, of general formula V represents a urethane having an $R^{14}$ corresponding to formula VIb.

Formula (V), specific (VIb)

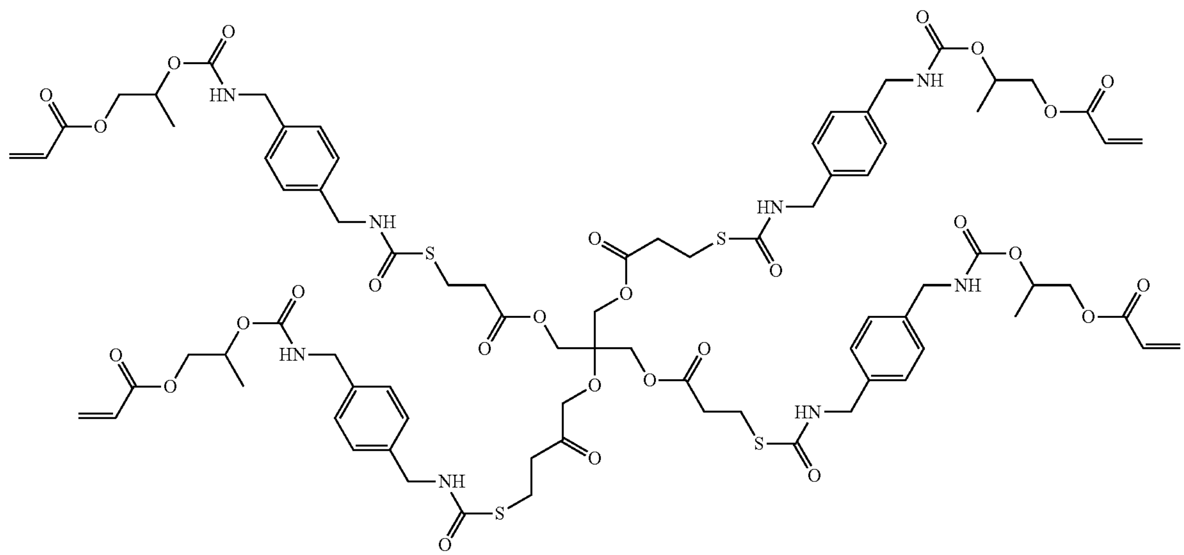

The urethanes of the formula V can be prepared, for example, from the reaction of, for example, di- to multi-functional thiols, such as thiol ethers or thiol esters of the exemplary structures 2b, 2c and 2d, with corresponding olefinic compounds containing isocyanate groups.

2b

2c

2d

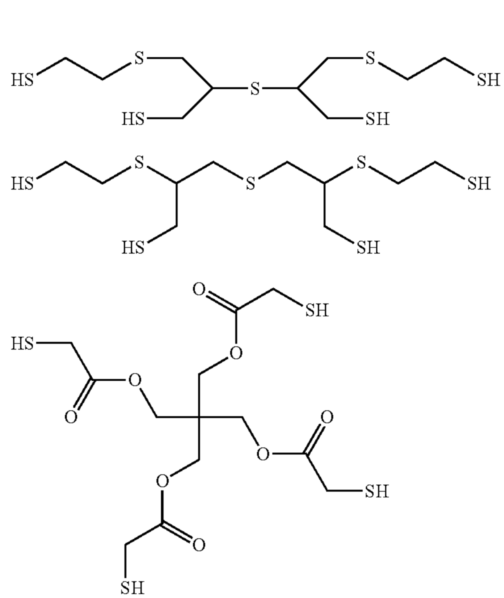

The polymerizable compositions comprise urethane acrylates, whereby the term urethane acrylates always also comprise urethane alkyl acrylates, such as urethane methacrylates, or an urethane acrylate without an alkyl group. In the present invention, acrylates are consequently taken together to include arcylates as well as methacrylates, so when a chemical compound is referred to as an acrylate in the present text, it always means the hitherto common designation(meth)acrylates, which includes both methacrylates and acrylates. The same applies to urethane acrylates (equivalent to urethane(meth)acrylates), which always includes urethane methacrylates and urethane acrylates. Alternatively, in the context of the present invention, urethane acrylates can thus also be described as urethane(meth) acrylates and acrylates as (meth)acrylates. The same applies accordingly to urethane(meth)acrylates containing thiolurethane groups (ii).

Furthermore, it is an object of the invention to provide a composition, in particular a dental composition, preferably a dental composite, in which the urethane acrylate of the general formula I and/or of the formula V in each case independently with $R^8$ comprises bivalent aromatic hydrocarbon having 6 to 12 C-atoms, divalent alicyclic hydrocarbon having 6 to 12 carbon atoms or divalent linear or branched alkylene having 6 to 12 carbon atoms or divalent linear or branched alkylene having an aromatic or alicyclic group, in particular a bicyclic or tricyclic group.

In the blends of urethanes of formulas I and V according to the invention, crystallization of pure monomer 1 is suppressed in this way by the presence of monomer 2. In this way, easier handling of the monomer blend/monomer mixture of 1 and 2 with mechanically similar properties to pure 1 results, as can be shown from the examples. A preferred mass ratio of the urethanes of formulas I and V, in particular with formula(s) VI, is preferably from 1:1 to 20:1, preferably the mass ratio is around 9:1, wherein the number 9 can vary with plus/minus 1. The mass ratio of formulas I to V can in principle be adjusted as desired.

According to a particularly preferred embodiment, a composition according to the invention comprises at least two urethane acrylates, in particular a mixture of at least these urethane acrylates, comprising at least one urethane acrylate of the formula I and the at least one second urethane acrylate having at least one bifunctional thiolurethane group and at least one olefinic group, these urethane acrylates being present in a mass ratio of from 1:1 to 100:1, in particular from 2:1 to 50:1, preferably from 5:1 to 20:1, more preferably from 7:1 to 10:1 ( ): 1+/−1. Furthermore, it is preferred if the at least two urethane acrylates comprising at least one urethane acrylate of formula I and at least one second urethane acrylate having at least one bifunctional thiolurethane group and at least one olefinic group are present in a molar ratio of from 1 to 2.5 to 0.0125 to 0.25, in particular from 0.5 to 1.25 to 0.0125 to 0.25.

The two urethane acrylate monomers 1 and 2 preferably have an aromatic and rigid center in combination with flexible aliphatic structures in the periphery of the molecular structures, resulting in a high mechanical strength of the thermoset polymer after free-radical polymerization of the monomer blend of 1 and 2, especially as component (ii) of the polymerizable composition. Due to the spatial size as well as the flexible aliphatic side chains in the periphery of the molecular structures in 1 and 2, especially of prepolymer 2, a comparatively low polymerization shrinkage of the monomer blend of 1 and 2 results. The high proportion of sulfur atoms as well as the high aromatic content in the molecular structure of the monomer blend of 1 and 2 also leads to a high transparency of the composite, which in turn results in a high depth of cure. In clinical practice, high transparency is also desirable for the manufacture of highly esthetic dental restorations. In addition, it was found that the use of the monomer blend of 1 and 2 leads to a comparatively high double bond turnover.

A particularly preferred second urethane acrylate having at least one bifunctional thiolurethane group and having at least one olefinic group has a structure of the general formula V,

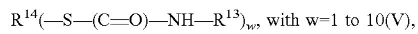

$R^{14}(—S—(C═O)—NH—R^{13})_w$, with w=1 to 10(V), wherein $R^{14}$ is a residue comprising at least mono- to deca-functional esters, ethers or thioethers, and wherein $R^{13}$ is a residue each independently selected from residues having at least one olefinic group. In particular, $R^{13}$ is $—R^8NH(C═O)OR^{10}O(C═O)CH═CH_2$, $—R^8NH(C═O)OR^{10}O(C═O)C(CH_3)═CH_2$. Preferably, $R^{13}$ is equal to formula VIII (VIII)

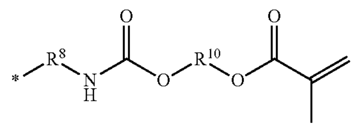

Formula V can also be represented as $R^{14}(—R^7)_w$, with w=1 to 10, preferably w=2 to 4, wherein $R^7$=—$R^8$NH—$R^{13}$. With $R^7$ equal to Formula VII (VII)

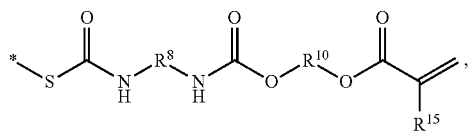

wherein $R^{15}$ is H or C1 to C4 alkyl, preferably —$CH_3$, wherein $R^8$ and $R^{10}$ are as defined above and below.

It is further preferred if in formula V the residue $R^{14}$ has one of the following structures VIa to VId VIa

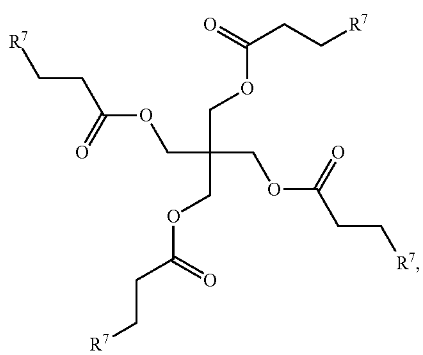

VIb

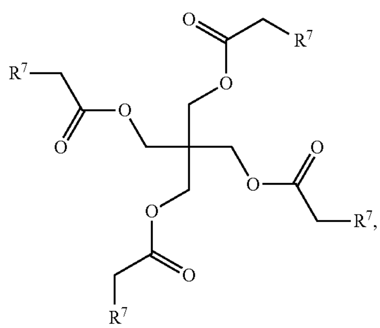

VIc

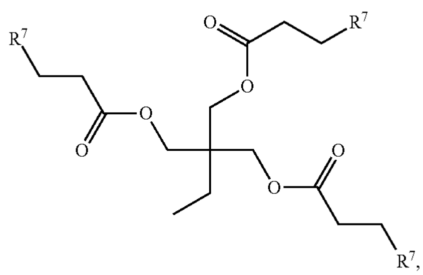

VId

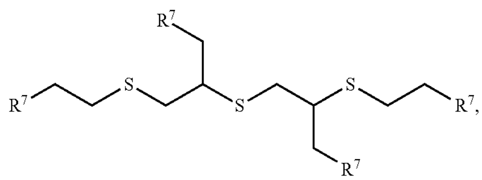

-continued

VIe

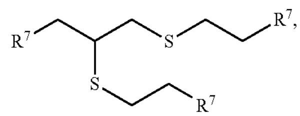

VIf

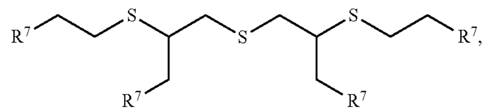

VIg

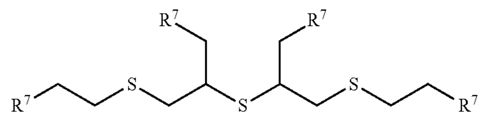

with $R^7$ in formula VIa to VIg each independently selected from (VII)

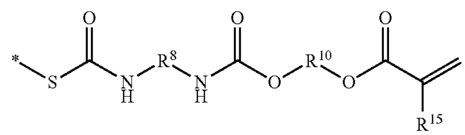

with $R^8$ in each case independently a divalent hydrocarbon group having 6 to 12 C-atoms, with $R^{10}$ in each case independently selected from linear C2 to C6 alkylene groups or linear C2 to C6 oxyalkylene groups, wherein $R^{10}$ optionally in each case independently has a C1-C3 alkyl group or (meth)acryloxymethylene group, and with $R^{15}$ in each case independently equal to H, C1 to C4 alkyl, in particular $CH_3$ or H.

With $R^8$ in each case independently in $R^7$ or formulas I, Ia, VII and VIII

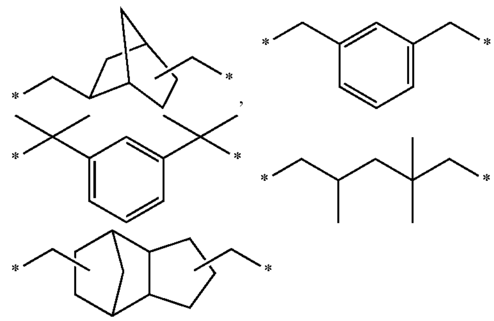

With, in each case independently, $R^{10}$ in $R^7$ or formulas VII and VIII, wherein the above alkylene and the oxyalkylene may also be present in inverted form as $R^{10}$ in $R^7$

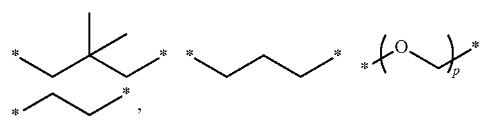

with p=1 to 8, preferably p=1 to 3

Particularly preferred urethane acrylates of the general formula I comprise:

I

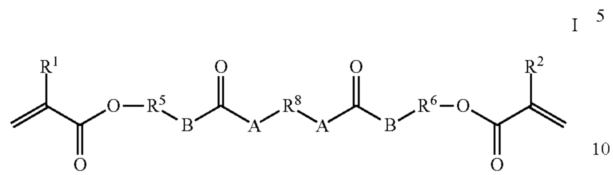

wherein A=O, when B=NH or A=NH, when B=O and wherein $R^1$=H or $CH_3$, $R^2$=H or $CH_3$, and $R^5$ and $R^6$ are each independently selected from linear C2 to C6 alkylene groups or linear C2 to C6 oxyalkylene groups, wherein $R^5$ and Re each optionally independently have a C1-C3 alkyl group or (meth)acryloxymethylene group, preferably $CH_3$ and $R^8$ comprises one of the following specific divalent groups

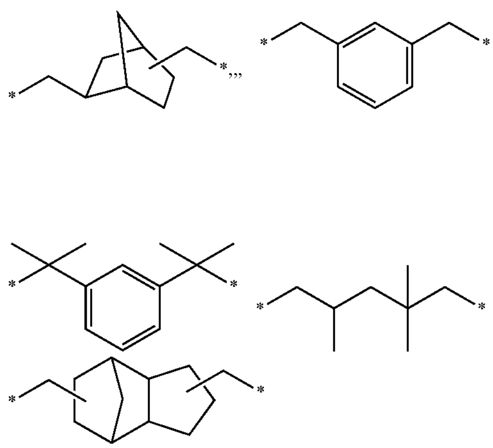

Particularly preferably, $R^5$ and $R^6$ are each independently selected from linear C2 to C6 alkylene groups or linear C2 to C6 oxyalkylene groups, wherein $R^5$ and $R^6$ optionally each independently comprise a C1-C3 alkyl group or (meth) acryloxymethylene group. Therefore, $R^5$, $R^6$ or even $R^{10}$ may each independently comprise: C2-6 alkylene group in which a hydrogen atom may be substituted with a C1-3 alkyl group or a (meth)acryloyloxymethylene group, or a linear oxyalkylene group in which a hydrogen atom may be substituted with a C1-3 alkyl group or a (meth)acryloyloxymethylene group. Preferably, the above alkyl groups are linear. Examples of linear alkylene groups include $-CH_2CH_2-$, $-CH_2CH_2CH_2-$, $-CH_2CH_2CH_2CH_2-$, $-CH_2CH_2CH_2CH_2CH_2-$, $-CH_2CH_2CH_2CH_2CH_2CH_2-$, with preference given to $-CH_2CH_2-$, $-CH_2CH_2CH_2-$, $-CH_2CH_2CH_2CH_2-$. Preferred linear oxyalkylene groups include $-CH_2CH_2OCH_2CH_2-$ and $-CH_2CH_2OCH_2CH_2OCH_2CH_2-$, preferably $-CH_2CH_2OCH_2CH_2-$. Likewise, the aforementioned groups may each have a hydrogen atom substituted against a methyl group or (meth)acryloxy group.

Preferred urethanes of the general formula I comprise the urethanes of the formulas Ia with Ia

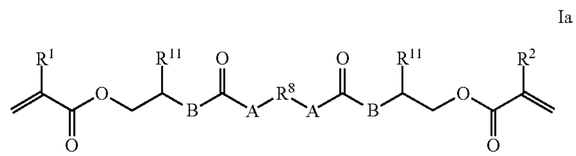

Each $R^{11}$ is independently H, C1-C3 alkyl groups or (meth)acryloxymethylene group, preferably H or $CH_3$. Here, both $R^{11}$ may be the same or different. With $R^8$ as defined above as specific groups.

Due to the comparatively high viscosity of monomers 1 and 2, the two urethane acrylate monomers and optionally other urethane acrylates require the addition of a reactive diluent as a monomer blend in order to adjust the processability of the composition, in particular as a dental composite.

Preferably, component (iii) of the at least one di-, tri-, tetra- or multi-functional monomer having at least one ether group, thioether group, at least one tri-functional triester and/or di-functional diester, the diester being selected from tricyclodecane dimethanol dimethacrylate and tricyclodecane dimethanol diacrylate or mixtures comprising at least two of these di-, tri-, tetra- or multi-functional monomers having a viscosity of less than or equal to 2000 mPas, preferably less than or equal to 1000 mPas, particularly preferably less than or equal to 500 mPas. The aforementioned monomers of component (iii) are preferably aliphatic and/or cycloaliphatic bis(meth)acrylates, with a viscosity of less than or equal to 2000 mPas, preferably less than or equal to 1000 mPas, particularly preferably less than or equal to 500 mPas. Examples of monomers of component (iii) that can be used in combination with the urethanes of component (ii) include, preferably triethylene glycol dimethacrylate, triethylene glycol diacrylate, tetraethylene glycol dimethacrylate, tetraethylene glycol diacrylate, tricyclodecane dimethanol dimethacrylate, tricyclodecane dimethanol diacrylate. Likewise, acrylate-functional thioethers or tri- or tetra-functional esters can be used as component (iii).

A combination with thioethers as component (iii) exhibits particularly high transparency combined with low shrinkage and a high double bond turnover. These properties are particularly advantageous in dental applications for the production of dental composites. Advantageously, each of the monomers of component (iii) has a viscosity of less than 2000 mPas, preferably less than 1000 mPas, particularly preferably less than 500 mPas.

Preferred di-, tri-, tetra- or multi-functional monomers with at least one thioether group, preferably as reactive diluents, are di- to multi-functional thio(meth)acrylate compounds. These are thioacrylates as well as thio(meth)acrylates which are characterized by an absence of aromatic groups, such as phenyl, phenylene or bisphenol-A, in the molecular structure. The preparation of acrylates containing thioether groups is disclosed in EP3795597A1, to which full reference is made.

The monomers in component (ill) comprising thioether groups may in particular comprise at least one of the following monomers or also mixtures of at least two of the monomers of component (ii). Particularly preferably, one or more of the following monomers 4 to 9 are used in component (ii).

4
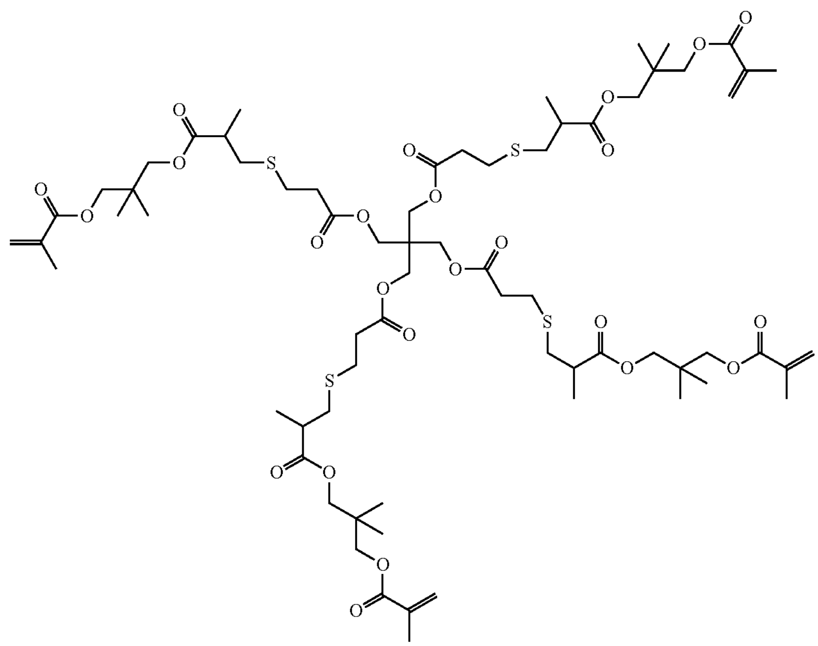
5
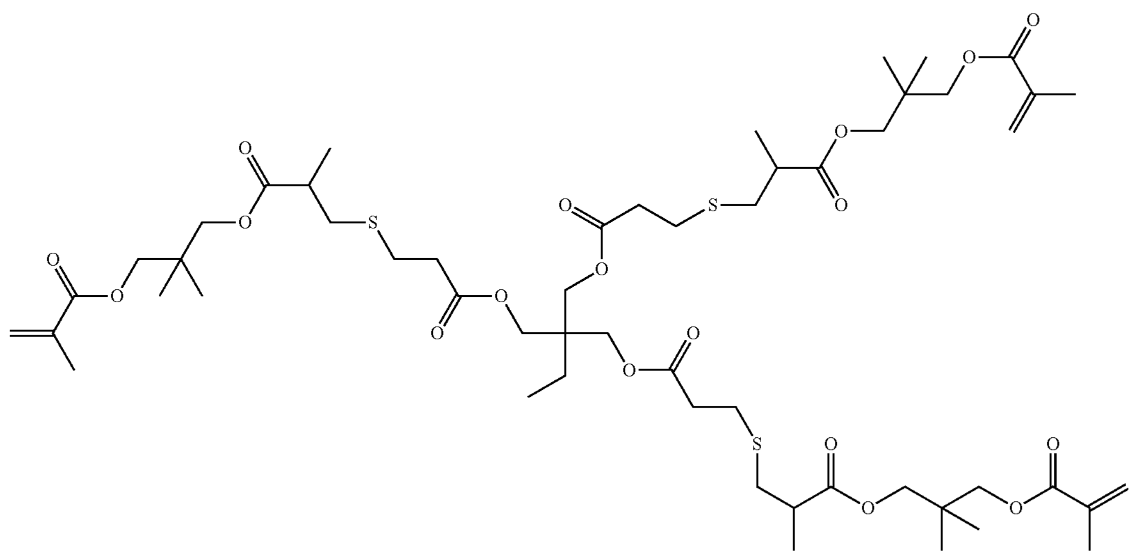
6
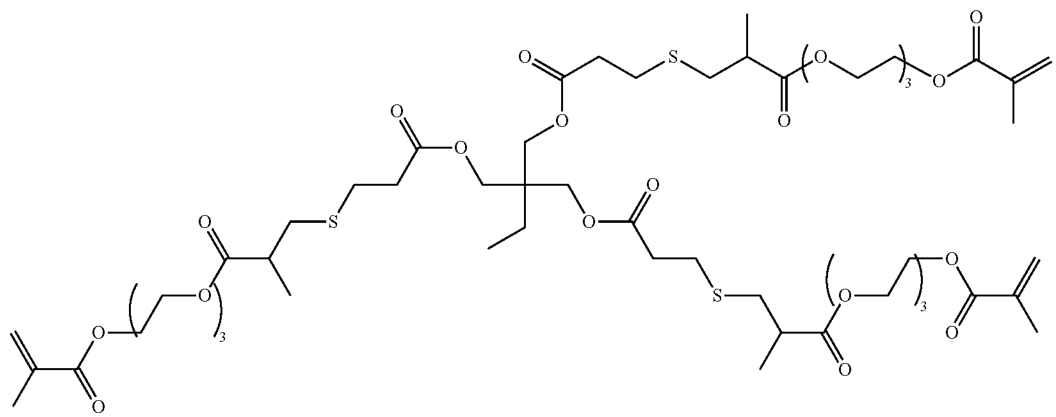

-continued

7

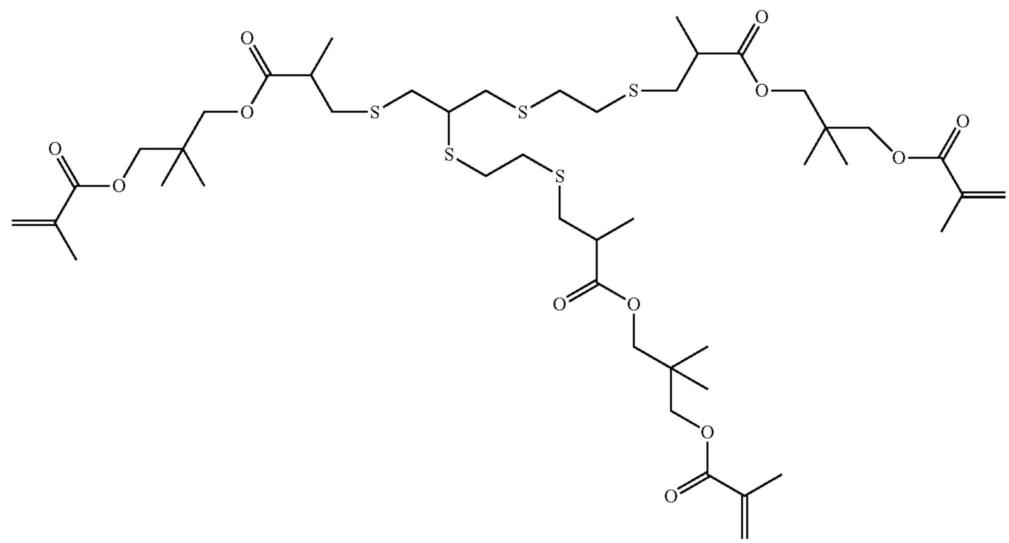

8

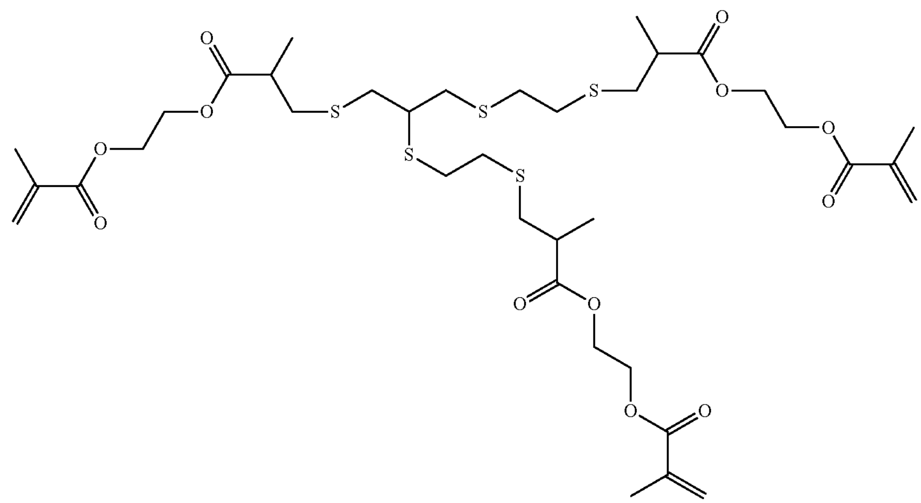

9

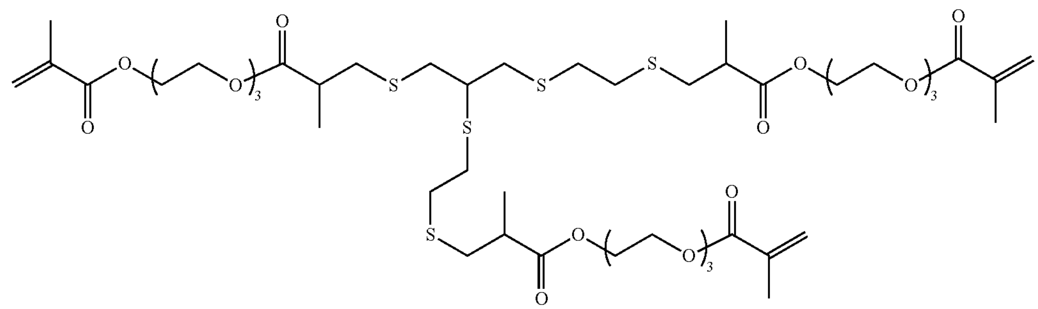

Due to the increased sulfur content in the molecular structure of the monomers containing thioether groups, in particular the thio(meth)acrylates, not only a low viscosity of the dental composite but also an increased transparency of the resulting composite, comprising at least two urethanes-monomers 1 and 2 as well as the monomers of component (iii), in particular the respective reactive diluents 4 to 9, is achieved. Compared to commercially available reactive diluents, the reactive diluents 4 to 9 as component (iii) have a high molecular weight, which leads to a comparatively low polymerization shrinkage.

Furthermore, the comparatively high molecular weight of reactive diluents 4 to 9 leads to lower brittleness of the polymerized composite, which can be determined on the basis of the ratio between E-modulus and flexural strength, as can be seen, for example, in the embodiment examples.

The monomers of component (ii), in particular the reactive diluents containing thioether groups or tri- or tetra-ester groups, can be used in combination with the monomer blend of 1 and 2, of formulas I and V, either individually or in mixtures with one another.

Particularly preferably, the polymerizable composition comprises as component (iii) at least one di-, tri-, tetra- or multi-functional monomer having at least one ether group of the formula III, thioether group of the formula IV and/or an at least tri- or tetra-functional triester of the formula II or mixtures of at least two of the monomers, in particular comprising at least one monomer of the formulas IIa, IIb, IIc, III, IVa, IVb, IVc and/or IVd (IIa)

(IIb)

(IIc)

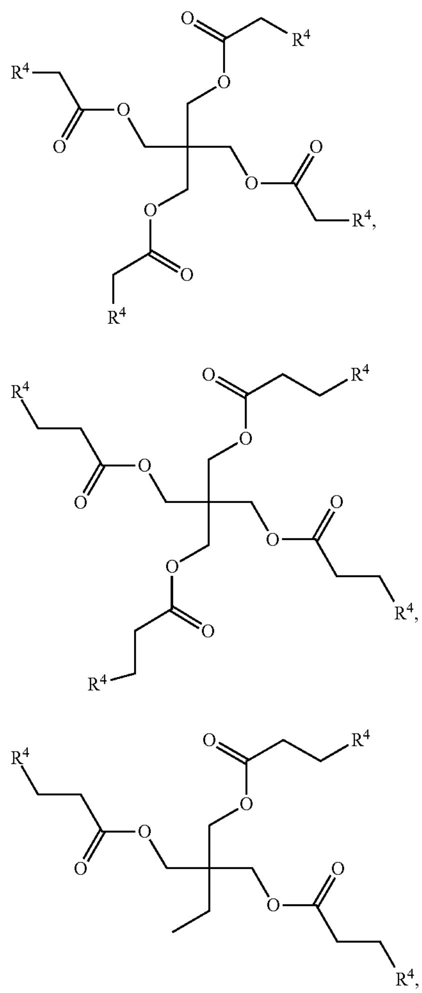

$$CH_2{=}C(CH_3)COO(CH_2CH_2O)_vCOC(CH_3){=}CH_2 \quad (III),$$

with v=3 to 20, in particular v=3 to 15, preferably v=3 to 8

(IVa)

(IVb)

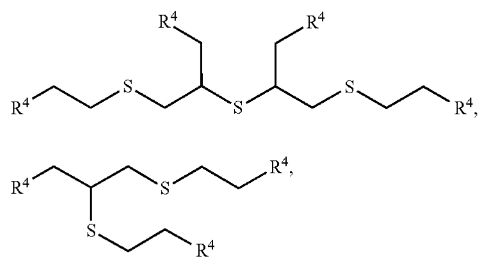

-continued (IVc)

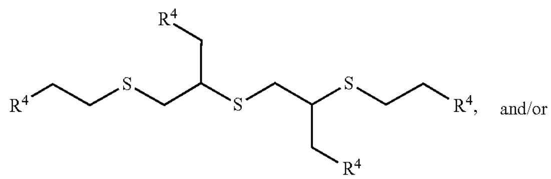

and/or (IVd)

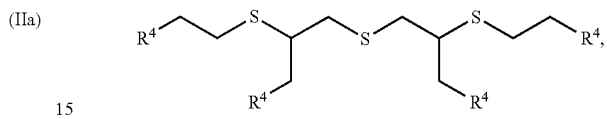

with in each case independently at formulas IIa, IIb, IIc, IVa, IVb, IVc, IVc and/or IVd with $R^4$=

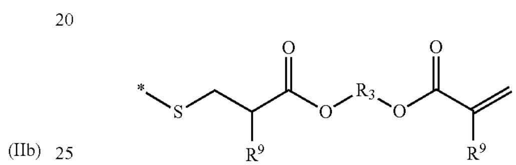

wherein in each case independently $R^9$=H or $CH_3$, and wherein $R^3$, wherein $R^3$ may be as shown below or may be inverted, $R^3$= selected from

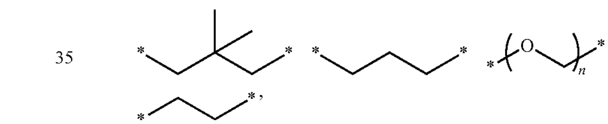

n=1 to 8, preferably n=3.

Particularly preferred compositions include:

(i) 5 to 40 wt.-%, in particular 5 to 30 wt.-%, of an inorganic filler component, in particular comprising at least one glass, in particular dental glass, silicate, metal oxide, mixed oxide, silicon dioxide, zirconium dioxide, zinc oxide and/or mixtures of at least two of the said components, the components having a mean particle size of 0.2 μm to 10 μm, and optionally at least one amorphous metal oxide having a mean primary particle size of 10 nm to 115 nm, and (ii) 60 to 85 wt.-% of at least two urethane acrylates, said urethane acrylates comprising at least one urethane acrylate of formula I and at least one second urethane acrylate having at least one bifunctional thiolurethane group and at least one olefinic group, (iii) 0.5 to 25 wt.-% of at least one di-, tri-, tetra- or multi-functional monomer having at least one ether group, thioether group and/or at least one tri-functional triester and/or di-functional diester, said diester being selected from tricyclodecanedimethanol dimethacrylate and tricyclodecanedimethanol diacrylate or mixtures of at least two of said di-, tri-, tetra- or multi-functional monomers, (iv) 0.01 to 10 wt.-% of at least one initiator, an initiator system, and optionally at least one stabilizer and optionally at least one pigment, wherein the total composition of the composition is 100 wt.-%.

Likewise, particularly preferred compositions include:

(i) 5 to 90 wt.-%, in particular 14.98 to 90 wt.-%, of an inorganic filler component, in particular comprising at least one glass, in particular dental glass, silicate, metal oxide, mixed oxide, silicon dioxide, zirconium dioxide, zinc oxide and/or mixtures of at least two of the said components, the components having a mean particle size of 0.2 μm to 10 μm, and optionally at least one amorphous metal oxide having a mean primary particle size of 10 nm to 115 nm, and (ii) 10 to 85 wt.-% of at least two urethane acrylates, said urethane acrylates comprising at least one urethane acrylate of formula I and at least one second urethane acrylate having at least one bifunctional thiolurethane group and at least one olefinic group.

(iii) 0.01 to 25 wt.-% of at least one di-, tri-, tetra- or multi-functional monomer having at least one ether group, thioether group and/or at least one tri-functional triester and/or di-functional diester, said diester being selected from tricyclodecanedimethanol dimethacrylate and tricyclodecanedimethanol diacrylate or mixtures of at least two of said di-, tri-, tetra- or multi-functional monomers, (iv) 0.01 to 10 wt.-% of at least one initiator, an initiator system, and optionally at least one stabilizer and optionally at least one pigment, wherein the total composition of the composition is 100 wt.-%.

An equally particularly preferred composition comprises (i) 40 to 90 wt.-% of an inorganic filler component, in particular comprising at least one glass, in particular dental glass, silicate, quartz, feldspar, metal oxide, mixed oxide, silicon dioxide, zirconium dioxide and/or zinc oxide having an average particle size of 0.4 μm to 10 μm, and optionally at least one amorphous metal oxide having an average primary particle size of 10 nm to 115 nm, as well as (ii) from 10 to 59.98 wt.-% of at least two urethane acrylates, said urethane acrylates comprising at least one urethane acrylate of formula I and at least one second urethane acrylate having at least one bifunctional thiolurethane group and at least one olefinic group, or a mixture of urethane acrylates of formulas I and V and optionally isomers of formula I, (iii) 0.01 to 15 wt.-% of at least one di-, tri-, tetra- or multi-functional monomer having at least one ether group, thioether group and/or at least one tri-functional triester and/or di-functional diester, said diester being selected from tricyclodecanedimethanol dimethacrylate and tricyclodecanedimethanol diacrylate or mixtures of at least two of said di-, tri-, tetra- or multi-functional monomers, (iv) 0.01 to 10 wt.-% of at least one initiator, an initiator system, and optionally at least one stabilizer and optionally at least one pigment, wherein the total composition of the composition is 100 wt.-%.

Other preferred compositions include:

(i) 50 to 90 wt.-% of an inorganic filler component, in particular comprising at least one glass, in particular dental glass, silicate, quartz, feldspar, metal oxide, mixed oxide, silicon dioxide, zirconium dioxide and/or zinc oxide having an average particle size of 0.4 μm to 10 μm, and optionally at least one amorphous metal oxide having an average primary particle size of 10 nm to 115 nm, as well as (ii) 20 to 49.98 wt.-% comprising at least two urethane acrylates, wherein the urethane acrylates comprise at least one urethane acrylate of formula I and at least one second urethane acrylate having at least one bifunctional thiolurethane group and at least one olefinic group, (iii) 0.01 to 15 wt.-% of at least one di-, tri-, tetra- or multi-functional monomer having at least one ether group, thioether group and/or at least one tri-functional triester and/or di-functional diester, said diester being selected from tricyclodecanedimethanol dimethacrylate and tricyclodecanedimethanol diacrylate or mixtures of at least two of said di-, tri-, tetra- or multi-functional monomers, (iv) 0.01 to 10 wt.-% of at least one initiator, an initiator system, and optionally at least one stabilizer and optionally at least one pigment, wherein the total composition of the composition is 100 wt.-%.

Particularly preferred compositions comprise (i) 60 to 85 wt.-% of an inorganic filler component, in particular comprising at least one glass, silicate, quartz, feldspar, metal oxide mixed oxide, silicon dioxide, zirconium dioxide and/or zinc oxide having an average particle size of 0.4 μm to 10 μm, and optionally at least one amorphous metal oxide having an average primary particle size of 10 nm to 115 nm, and (ii) 10 to 39.98 wt.-% of at least two urethane acrylates, the urethane acrylates comprising at least one urethane acrylate of formula I and at least one second urethane acrylate having at least one bifunctional thiolurethane group and at least one olefinic group, or a mixture of urethane acrylates of formulas I and V and optionally isomers of formula I, (iii) 0.01 to 15 wt.-% of at least one di-, tri-, tetra- or multi-functional monomer having at least one ether group, thioether group and/or at least one tri-functional triester and/or di-functional diester, said diester being selected from tricyclodecanedimethanol dimethacrylate and tricyclodecanedimethanol diacrylate or mixtures of at least two of said di-, tri-, tetra- or multi-functional monomers, (iv) 0.01 to 10 wt.-% of at least one initiator, an initiator system, and optionally at least one stabilizer and optionally at least one pigment, wherein the total composition of the composition is 100 wt.-%.

Generally preferred (ii) urethanes comprise urethanes of formula I and optionally of formula V with VII and/or mixtures of these urethanes of formula I and optionally mixtures of the isomers of the aforementioned compounds with $R^1$, $R^2$ and $R^{15}$ each independently selected from H and alkyl having 1 to 8 C-atoms, particularly preferably $R^1$, $R^2$ and $R^{15}$ are H or $CH_3$.

Particularly preferred urethane acrylates of formula I or mixtures of urethane acrylates comprise urethanes of formula I and optionally mixtures of isomers, with $R^1$, $R^2$, $R^8$ and $R^{11}$ as defined above, Ib

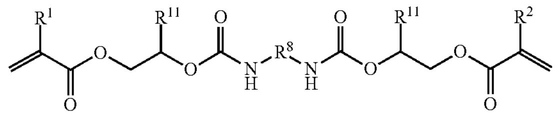

Ic

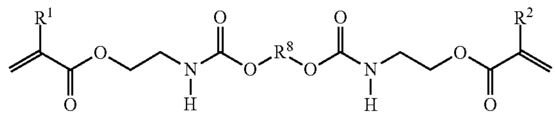

Quite preferably, urethane acrylates of formula I comprise at least one compound of formula Ic to Io and/or mixtures thereof and optionally mixtures of isomers thereof, and/or mixtures of these urethanes of formula I and optionally mixtures of the isomers of the above-mentioned compounds with $R^1$ and $R^2$ each independently selected from H and alkyl having 1 to 8 carbon atoms, Ic
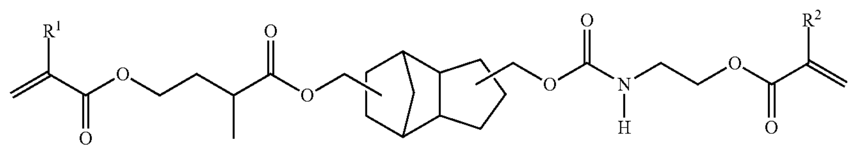
Id
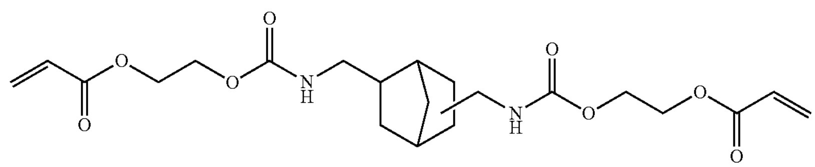
Ie
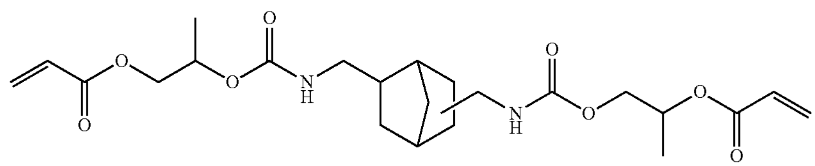
If
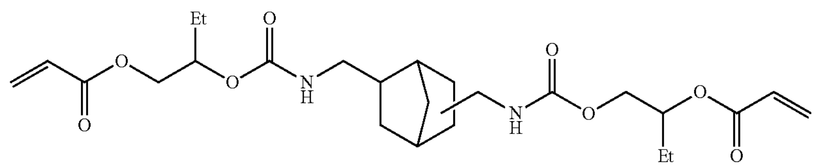
Ig
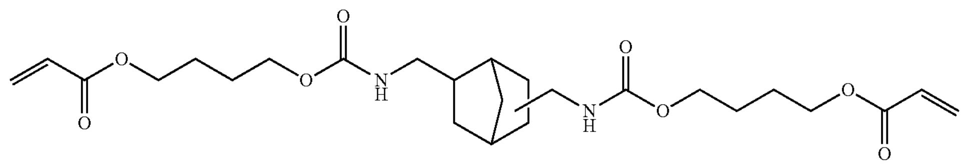
Ih
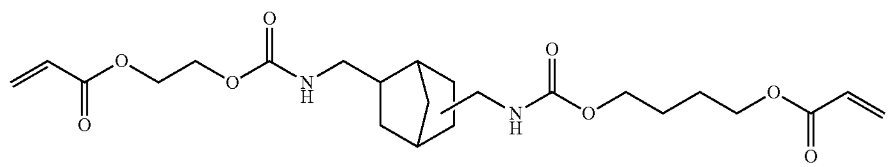
Ii
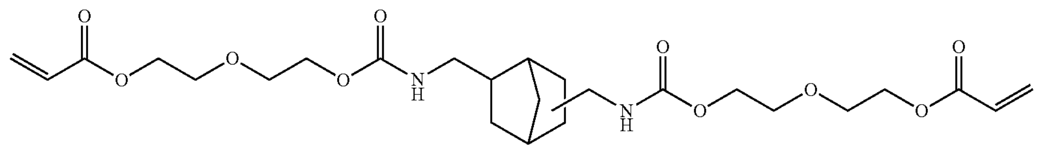
Ij
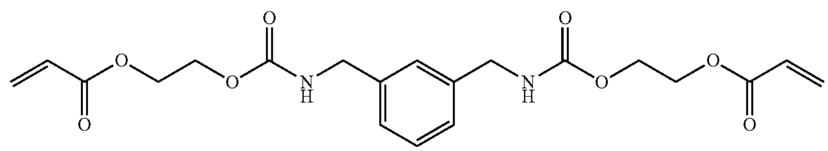
Ik
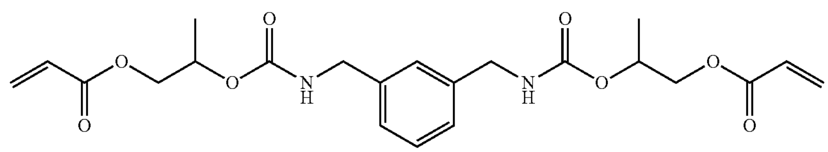
Il
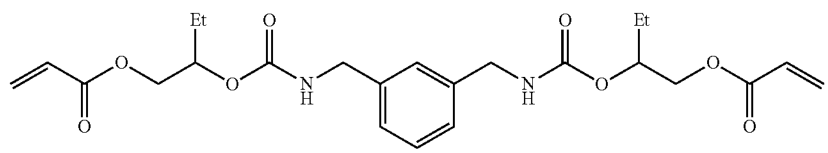

-continued

Im

In

Io

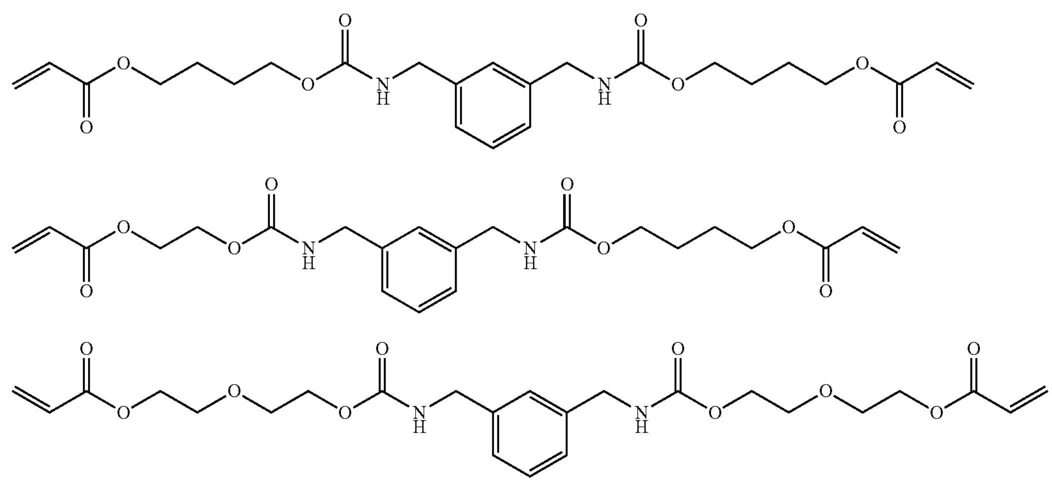

Also preferred are compositions having (iii) from 0.01 to 15 wt.-% of at least one di-, tri-, tetra-, or multi-functional monomer, wherein the total composition of the composition is 100 wt.-%.

According to one embodiment, the compositions may comprise at least one inorganic filler component comprising at least one glass, silicate, feldspar, metal oxide, mixed oxide, silicium dioxide, zirconia with a mean particle size $d_{50}$ of 0.5 to 10 μm. Alternatively preferred are compositions comprising a) at least one inorganic filler component comprising at least one glass, silicate, quartz, feldspar, metal oxide, mixed oxide, silica, zirconia or a mixture comprising at least two of the components having a mean particle size of $d_{50}$ of 1.8 μm, and preferably $d_{99}$ less than or equal to 20 μm, or b) comprises at least one inorganic filler component comprising at least one glass, feldspar, metal oxide, mixed oxide, silica, zirconia or a mixture comprising at least two of said components as a mixture of different fractions having an average particle size with i) $d_{50}$ from 2 to 8 μm, ii) $d_{50}$ from 1.0 to 2.0 μm, and iii) $d_{50}$ from 0.5 μm to 2 μm, the fractions of i) to ii) to iii) being in the ratio of 1 to 4:1:4 to 8, in particular from 2 to 3:1:6 to 7.

Further, the compositions may comprise as the amorphous metal oxide at least one non-agglomerated amorphous metal oxide having a primary particle size of from 2 to 150 nm, and wherein the amorphous metal oxide optionally comprises precipitated silica, fumed silica, zirconia, or mixed oxides.

Particularly preferably, the compositions comprise as (i) inorganic filler component (i.1) 0.005 to 85 wt.-%, in particular 50 to 85 wt.-%, of at least one glass, silicate, quartz, feldspar, metal oxide, mixed oxide, silica, zirconia or a mixture comprising at least two of these filler components, and optionally (i.2) comprises 0.005 to 5 wt.-%, in particular 0.05 to 2 wt.-%, of amorphous metal oxide, in particular fumed silica and/or precipitated silica, in particular 0.1 to 90 wt.-%, in particular 50.005 to 90 wt.-% of filler component, with respect to the total composition of the composition of 100 wt.-%.

Equally preferred compositions may comprise as (iii) monomers selected from di-methacrylic esters of polyethers, tri-, tetra- or multi-functional methacrylic esters of polyethers and 2,2-bis-[4-(2-hydroxy-3-methacryloyloxy-propoxy)phenyl]-propane, bis-(2'-oxa-3'-oxo-pentyl-4'-ene)-tetrahydrodicyclopentadiene, diesters of thioethers, triesters comprising tricyclodecane, and isomers thereof, and optionally pentaerythritol tetrapropoxyacrylate. Components (iii) may preferably comprise dimethacrylate polyethylene glycol, dimethacrylate polypropylene glycol. Dimethacrylate triethylene glycol (TEGDMA), diethylene glycol dimethacrylate (DEGMA) and dimethacrylate tetraethylene glycol (TEDMA) are particularly preferred.

In addition, a composition may comprise as (v) 0.01 to 15 wt.-% of a polymeric particulate filler, wherein the total composition of the composition is 100 wt.-%.

Preferred stabilizers include water, at least one benzophenone derivative and/or at least one phenol derivative.

Also subject to the invention are polymerized compositions, in particular obtained or obtainable by polymerization of one of the polymerizable compositions, wherein the polymerized compositions comprise

- 0.01 to 90 wt.-% of at least one inorganic filler component,
- 5 to 99.98 wt.-% of at least one polymer, in particular co-polymer, based on the polymerization of at least monomers and/or prepolymers
- comprising at least two urethane acrylates, wherein at least one urethane acrylate of formula I, as defined above and below, is having a divalent hydrocarbon group
- and the second urethane acrylate has at least one bifunctional thiolurethane group and at least one olefinic group, and/or mixtures of urethane acrylates comprising these, and
- at least one di-, tri-, tetra- or multi-functional monomer having at least one ether group, thioether group, at least one tri-functional triester and/or di-functional diester, said diester being selected from tricyclodecanedimethanol dimethacrylate and tricyclodecanedimethanol diacrylate or mixtures of at least two of said di-, tri-, tetra- or multi-functional monomers, and
- 0 to 10 wt.-%, in particular 0.01 to 10 wt.-%, preferably 0.01 to 10 wt.-%, of at least one pigment, the total composition of the polymerized composition being 100 wt.-%.

It is also an object of the invention to provide a polymerized composition obtained or obtainable by polymerizing the composition i) with a UV and/or Vis radiation source, preferably with a Vis radiation source having emission maxima in the spectral range from 380 nm to 530 nm, preferably with at least one maximum or maxima in the spectral range from 400 to 500 nm and/or thermal polymerization ii) at a pressure of 50 to 300 MPa and/or elevated temperature, preferably at 90 to 150° C.

In this context, the polymerized composition is preferably present in the form of a material block, in particular the material block is present as a three-dimensional geometric shaped body, in particular as a milled blank without an adapter or as a milled blank with an adapter for fixing in an automated material-removing device.

Most preferably, the composition is for use as a dental material, particularly as a fissure sealant, dental composite material, direct adhesive dental restoration, hoof repair material, bone cement, or bone cement for cementing artificial joint prostheses.

It is further an object of the invention to use a polymerizable composition, in particular as a dental composite material, preferably in additive manufacturing processes, in radiation-based generative manufacturing processes, in a stereolithography process, SLA process (laser-based stereolithography process), a DLP process (digital light processing) or an SLA and DLP process, in generative LED beamer-based manufacturing processes, in radiation- and thermal-based generative manufacturing processes, in thermal generative manufacturing processes, in 3D printing processes, multitjet processes (MJM) or polyjet processes, and/or b) for the manufacture of dental prosthetic restorations, orthodontic appliances and/or instruments in a material-removing process, in particular in a process in which the polymerized composition is removed by means of milling, cutting, polishing, breaking, flaking and/or drilling, in particular in a process in which the polymerized composition is removed by means of laser energy.

Also, an object of the invention is a use of a polymerizable composition in radiation-based polymerization processes, in particular UV and/or VIS polymerization processes, radical-induced polymerization processes, thermal-based polymerization processes and/or redox-based polymerization processes.

An object of the invention is the use of a polymerizable or a polymerized composition for the manufacture of dental prosthetic restorations comprising crowns, inlays, onlays, superstructures, artificial teeth, dental bridges, dental bars, spacers, abutments, veneers, or for making a bite splint, milling blank, dental prosthesis, part of a surgical prosthesis, drill guide, implant, mouthguard, joint prosthesis, telescope, implant part, orthodontic appliance, instrument or hoof part.

In combination with the monomer blend of 1 and 2 and in combination with the reactive diluents of component (iii) comprising at least one of monomers 4 to 9, triethylene glycol dimethacrylate, triethylene glycol diacrylate, tetraethylene glycol dimethacrylate, tetraethylene glycol diacrylate, tricyclodecane dimethanol dimethacrylate, tricyclodecane dimethanol diacrylate or mixtures of at least two of the monomers, all commercially available photoinitiators can be used. Preferably, a combination of camphorquinone with 2-ethylhexyl-4-dimethyl-aminobenzoate (EHA) is used in the composition. Likewise, peroxides or hydroperoxides, for example, as well as redox initiators for auto- or cold polymerization can be used for thermal polymerization. When redox initiators are used, the composition is formulated as a 2K composition that polymerizes only after mixing the two components.

In the present context, a thermally polymerizable composition is understood to mean a composition that can be polymerized at 60 to 150° C. or higher, preferably at 70 to 150° C. or higher, and particularly preferably from 90 to 150° C. According to the invention, it is further preferred if the volume shrinkage is small.

It is also an object of the invention to provide a dental composite material obtainable by polymerization i) with a UV/Vis radiation source, preferably with a Vis radiation source having emission maxima in the spectral range of 380 nm to 530 nm, preferably with at least one maximum or maxima in the spectral range of 400 to 500 nm, and optionally ii) at a pressure of 50 to 300 MPa and/or elevated temperature, preferably at 90 to 150° C., or i) with a UV and/or Vis radiation source, preferably with a Vis radiation source with emission maxima in the spectral range from 380 nm to 530 nm, preferably with at least one maximum or maxima in the spectral range from 400 to 500 nm and/or ii) at a pressure of 50 to 300 MPa and/or elevated temperature, preferably at 90 to 150° C.

The polymerizable compositions may also contain other additives, such as stabilizers, colorants and pigments, microbiocidal agents, fluoride ion-donating additives, optical brighteners, plasticizers and/or UV absorbers, inhibitors and UV stabilizers.

The following glasses, in particular dental glasses, are preferably suitable: aluminum silicate glasses or fluoroaluminum silicate glasses, fluoroaluminum silicate glasses containing boron, barium aluminum silicate, strontium silicate, strontium borosilicate, calium silicate, calcium borosilicate, sodium silicate glass, potassium silicate glass, lithium silicate and/or lithium aluminum silicate, as well as mixtures of at least two of the above-mentioned glasses. Amorphous spherical fillers based on oxide or mixed oxide, such as amorphous $SiO_2$, $ZrO_2$ or mixed oxides of $SiO_2$ and $ZrO_2$, can be used as amorphous metal oxide or as a mixture of amorphous metal oxides. Alternatively, mixed oxides of zirconia and silica, zirconia or zinc oxide as well as crystalline silicates can be used as filler components in the composition. All fillers, such as glasses, amorphous metal oxides or also x-ray opaques and/or pigments are preferably functionally silanized. In particular, thiol-, vinyl-, allyl-, norborn-2-enyl-, methacryl- or alkyne-functionalized silanes can be considered as silanes. Thus, the invention also covers compositions comprising fillers functionally silanized with thiol-, vinyl-, allyl-, norborn-2-enyl-, methacryl- or alkyne-functionalized silanes.

Further in each case preferably in combination with an amorphous silicon dioxide with 4 to 7.5 wt % in the total composition. The amorphous metal oxide is preferably a non-agglomerated amorphous metal oxide of a primary particle size of from 2 to 150 nm, in particular from 2 to 100 nm, preferably from 2 to 45 nm, wherein the amorphous metal oxide comprises silicon dioxide, precipitated silicon dioxide, fumed silica, zirconium oxide, mixed oxides or mixtures thereof, in particular the metal oxides are silanized. Suitable silanizing agents include (meth)arcyloxyalkyl-functional silanes or other alkyl- or olefin-functionalized silanes.

According to one embodiment, fillers for the preparation of dental composites can be added to the compositions. Particularly suitable are fillers based on oxides with a particle size of 0.4 μm to 20 μm, such as $SiO_2$, $ZrO_2$ and $TiO_2$ or mixed oxides of $SiO_2$, $ZrO_2$, ZnO and/or $TiO_2$. In addition, nanoscale or microfine fillers with a particle size of 0.01 to 500 nm are used, such as fumed silica or precipitated silica. Likewise, dental glasses and/or tectosilicates with a particle size of 0.4 μm to 20 μm and/or 0.01 mm to 15 mm, such as quartz powder, glass-ceramic powder and/or feldspar powder or x-ray opaque dental glass powders of, for example, barium or strontium aluminosilicate glasses, and x-ray opaque fillers with a particle size of 0.4 μm to 20 μm and/or 0.01 mm to 15 mm can be used as fillers. This can also be ytterbium trifluoride, tantalum (V) oxide, barium sulfate or mixed oxides of $SiO_2$ with ytterbium (III) oxide or tantalum (V) oxide, in particular of the above-mentioned particle sizes of 0.4 μm to 20 μm and/or 0.01 mm to 15 mm. All particle sizes mentioned are weight-average particle sizes, as in particular as $D_{50}$.

To improve the bond between the filler particles and the crosslinked polymer matrix, $SiO_2$-based fillers can be surface modified with thiol-, vinyl-, allyl-, norborn-2-enyl-, methacryl- or alkyne-functionalized silanes.

Examples of such silanes are 3-thio-propyltrimethoxysilane, 3-allyltriethoxysilane, methacryloxypropyltrimethoxysilane or N-[3-(triethoxysilyl)-propyl]-carbamic acid propargyl ester. Functionalized acid phosphates, such as 10-methacryloyloxydecyl dihydrogen phosphate, can also be used for surface modification of non-silicate fillers such as $ZrO_2$ or $TiO_2$.

In a preferred alternative, the composition may comprise, in addition to the inorganic filler component, a content of a polymeric particulate filler. The total content of such a polymeric particulate filler may be from 0.01 to 15 wt.-%, preferably from 0.5 to 10 wt.-% in the total composition of the composition of 100 wt.-%. The particle sizes of the polymeric filler are preferably in the range from 10 to 200 micrometers, in particular from 30 to 90 micrometers, more preferably from 20 to 50 micrometers.

In the present invention, the term acrylate includes (alkyl) acrylate or (meth)acrylate or urethane (alkyl) acrylate with (alkyl) in parentheses or urethane(meth)acrylate with (meth) in parentheses means that the term may include acrylates or urethane acrylates with and without alkyl groups or methyl group. The alkyl groups preferably comprise 1 to 10 C-atoms, preferably 1 to 2 C-atoms in said urethane alkyl acrylates. The alkyl groups preferably comprise 1 to 10 C-atoms, preferably 1 to 2 C-atoms in said (alkyl) acrylates.

Component (ii) comprising at least two urethane acrylates may additionally comprise at least one difunctional urethane acrylate, urethane (alkyl) acrylate, urethane (alkyl) acrylate having a divalent alkylene group or urethane(meth)acrylate having a divalent alkylene group, which is preferably selected from linear or branched urethane dimethacrylates functionalized with a divalent alkylene group, urethane dimethacrylate functionalized polyethers with alkylene group(s), such as bis(methacryloxy-2-ethoxycarbonylamino)alkylene, bis(methacryl-oxy-2-ethoxycarbonylamino) substituted polyalkylene ethers, preferably 1,6-bis(methacryloxy-2-ethoxycarbonylamino)-2,4,4-trimethyl hexane, UDMA with alternative designation HEMA-TDMI. Preferred is a bis(methacryloxy-2-ethoxycarbonylamino)alkylene, wherein alkylene comprises linear or branched C3 to C20, preferably C3 to C6, as particularly preferred is an alkylene substituted with methyl groups, such as HEMA-TMDI. The divalent alkylene preferably comprises 2,2,4-trimethylhexamethylene and/or 2,4,4-trimethylhexamethylene. Further, component (ii) may comprise di-HEMA-trimethylhexyl dicarbamate, diurethane dimethacrylate, a methacrylate adduct, urethane dimethacrylate.

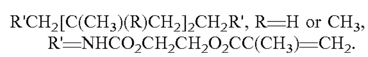

$R'CH_2[C(CH_3)(R)CH_2]_2CH_2R'$, R=H or $CH_3$, $R'=NHCO_2CH_2CH_2O_2CC(CH_3)=CH_2$.

Water can be added to the composition as a stabilizer to improve the consistency and flow behavior for processability. Preferably, stabilizers are added to the composition to prevent premature polymerization and to impart some shelf life to the material. As preferred stabilizers, the composition comprises in component (iv) at least one stabilizer selected from water, at least one benzophenone derivative, preferably alkoxy substituted benzophenone and/or phenol derivative, such as 2-hydroxy-4-methoxybenzophenone, 2,6-bis(1,1-dimethyl)-4-methylphenol, or a mixture of the three stabilizers. Preferably, the stabilizers are present from 0.01 to 10 wt.-% in the total composition, more preferably from 0.7 to 10 wt.-%, especially from 0.5 to 2 wt.-%. Furthermore, it is preferred if the composition contains 0.01 to 2 wt.-% of water as stabilizer, preferably 0.1 to 1.0 wt.-% of water.

For optimal adjustment of the color and aesthetics of the polymerized composition, at least one pigment comprising at least one fluorescent pigment and optionally at least one organic color pigment and/or at least one inorganic color pigment, such as titanium dioxide, in particular non-fluorescent color pigments, may be added. The at least one fluorescent pigment is preferably an organic fluorescent pigment, in particular a non-polymerizable organic fluorescent pigment optionally comprising aryl carboxylic acid esters, aryl carboxylic acids, coumarin, rhodamine, naphthanlinimide or a derivative of the respective substance. Inorganic fluorescent pigments may include $CaAl_4O_7$: $Mn^{2+}$, $(Ba0.98Eu0.02)MgAl_{10}O_{17}$, $BaMgF_4$: $Eu^{2+}$, Y (1.995) Ce (0.005) $SiO_5$.

As pigments, in particular colored pigments, the composition may comprise organic pigments as well as inorganic pigments, in particular comprising diethyl-2,5-dihydroxyterephthalate, N,N'-bis(3,5-xylyl) perylene-3,4:9,10-bis(dicarbimide), copper phthalocyanine, titanate pigment, in particular chromium antimontitanate (rutile structure), spinel black, in particular pigments based on iron oxide black ($Fe_3O_4$), wherein iron (Fe) is partially substituted by chromium and copper or nickel and chromium or manganese, zinc iron chromium spinel, brown spinel, ((Zn,Fe) $(Fe,Cr)_2O_4$) cobalt zinc aluminate blue spinel and/or titanium oxide. The pigments comprising fluorescent and colored pigments are preferably present from 0.01 to 10 wt.-% in the total composition, more preferably from 0.01 to 5 wt.-%, more preferably from 0.01 to 1 wt.-%.

According to another preferred embodiment, the composition may comprise:

(iv) 0.01 to 2 wt.-% of photoinitiator for the UV and/or Vis region or a photoinitiator system for the UV and/or Vis region, and 0.01 to 2 wt.-% of stabilizer.

Furthermore, the polymerized composition can be used for the production of technical components that are particularly exposed to high mechanical stresses, such as plastic templates, nails, screws as well as other components familiar to the skilled person, etc.

The following are also preferably suitable as additional urethane(meth)acrylates of component (ii): at least one urethane(meth)acrylate, in particular a urethane dimethacrylate, preferably a bis(methacryloxy-2-ethoxycarbonylamino)alkylene, diurethane acrylate oligomers, alkyl-functional urethane dimethacrylate oligomers, aromatic-functionalized urethane dimethacrylate oligomers, aliphatic unsaturated urethane acrylates, Bis(methacryloxy-2-ethoxycarbonylamino) substituted polyethers, aromatic urethane diacrylate oligomers, aliphatic urethane diacrylate oligomers, aliphatic urethane diacrylates, hexafunctional aliphatic urethane resins, aliphatic urethane triacrylate, aliphatic urethane acrylate oligomer, unsaturated aliphatic urethane acrylates. Preferred are difunctional and polyfunctional urethane (meth)acrylates, such as in particular urethane di(meth) acrylates, particularly preferred is the at least one (iii) urethane dimethacrylate selected from linear or branched alkyl functionalized urethane dimethacrylates, urethane dimethacrylate functionalized polyethers, in particular bis (methacryloxy-2-ethoxycarbonylamino)alkyls, bis(methacryloxy-2-ethoxycarbonylamino) substituted polyethers, preferably 1,6-bis(methacryloxy-2-ethoxycarbonylamino)-2,4,4-trimethylhexanes. Suitable urethane(meth)acrylates are available under the following brand names: Ebecryl 230 (aliphatic urethane diacrylate), Actilane 9290, Craynor 9200 (di-urethane acrylate oligomer), Ebecryl 210 (aromatic urethane diacrylate oligomer), Ebecryl 270 (aliphatic urethane diacrylate oligomer), Actilane 165, Actilane 250, Genomer 1122 (monofunctional urethane acrylate), Photomer 6210 (Cas No. 52404-33-8, aliphatic urethane diacrylate), Photomer 6623 (hexafunctional aliphatic urethane resin), Photomer 6891 (aliphatic urethane triacrylate), UDMA, Roskydal LS 2258 (aliphatic urethane acrylate oligomer), Roskydal XP 2513 (unsaturated aliphatic urethane acrylate). The urethane(meth)acrylates can preferably be selected from the aforementioned urethane(meth)acrylates or from mixtures of at least two different, preferably at least three different aforementioned urethane(meth)acrylates.

The at least one di-, tri-, tetra- or multi-functional monomer of component (iii), may further comprise at least one of the following monomers, in particular a mixture of monomers comprising bis-(2'-oxa-3'-oxo-pentyl-4'-ene)tetrahydrodicyclo pentadiene and isomers thereof, 1,4-butanediol dimethacrylate (1,4-BDMA) or pentaerythritol tetraacrylate, decanediol di(meth)acrylate, dodecanediol di(meth)acrylate, hexyldecanediol di(meth)acrylate, trimethylol propantri (meth)acrylate, pentaerythritol tetra(meth)acrylate, and butanediol di(meth)acrylate, ethylene glycol di(meth)acrylate, a mixture containing at least one of these (meth) acrylates and/or copolymers comprising one or at least two of the abovementioned monomers.

In addition to the di-, tri- or multi-functional monomer or monomers, at least one of the following monomers may be present in the composition comprising at least one monomer, in particular a mixture of monomers of methyl methacrylate, ethyl methacrylate, propyl methacrylate, butyl methacrylate, n-hexyl methacrylate, 2-phenoxyethyl methacrylate, isobornyl methacrylate, isodecyl methacrylate, polypropylene glycol mono methacrylate, tetrahydrofuryl methacrylate, Methyl acrylate, ethyl acrylate, propyl acrylate, butyl acrylate, n-hexyl acrylate, 2-phenoxyethyl acrylate, isobornyl acrylate, isodecyl acrylate, tetrahydrofurylacrylate, hydroxyethyl acrylate, hydroxypropyl acrylate, hydroxyethyl methacrylate, hydroxypropyl methacrylate, benzyl acrylate, furfuryl acrylate or phenyl(meth)acrylate, a mixture containing at least one of these (meth)acrylates and/or copolymers comprising one or at least two of the abovementioned monomers.

Furthermore, it is an object of the invention to provide a composition which preferably additionally contains at least one or more substances from the groups of fillers, pigments, stabilizers, regulators, antimicrobial additives, UV absorbers, thixotropic agents, catalysts and crosslinkers. Such additives—as well as pigments, stabilizers and regulators—are used in rather small amounts, e.g. a total of 0.01 to 3.0, especially 0.01 to 1.0 wt.-% based on the total composition of the formulation. Suitable stabilizers are, for example, hydroquinone monomethyl ether or 2,6-di-tert.-butyl-4-methylphenol (BHT).

As component (iv), the composition preferably comprises from 0.01 to 10 wt.-%, in particular from 0.5 to 5 wt.-%, preferably from 0.5 to 2 wt.-%, of at least one initiator or initiator system, preferably i) at least one photoinitiator for the UV and/or Vis range or a photoinitiator system for the UV and/or Vis range and optionally at least one stabilizer, and optionally further customary additives, optionally pigment(s) or dye(s).

Particularly preferred photoinitiators include alpha-hydroxyphenyl ketone, benzildimethyl ketal or 2,4,6-trimethylbenzoyl diphenyl phosphine oxide, phenyl bis(2,4,6-trimethylbenzoyl) phosphine oxide, 2,4,6-trimethylbenzoyl phenyl phosphinic acid ethyl ester, and mixtures of at least two of the photoinitiators, bisacyl phosphine oxides (BAPO). Or also camphorquinone with amines selected from N,N-dimethyl-p-toluidine, N-N-dihydroxyethyl-p-toluidine and p-dimethylaminobenzoic acid diethyl ester.

Typical stabilizers include 2,6-di-tert.-butyl-4-methylphenol (BHT) or hydroquinone monomethyl ether (MEHQ), 2-hydroxy-4-methoxybenzophenone, HALS (hindered amine light stabilizers), benzotriazole ultraviolet absorbers (UVAs) and hydroxy phenyl triazines (HPT). Particularly suitable stabilizers include e.g. hydroquinone monomethyl ether or 2,6-di-tert.-butyl-4-methylphenol (BHT).

Suitable initiators, in particular thermal initiators or initiator systems, are peroxides, hydroxyperoxides, optionally azo compounds, or mixtures comprising these. Suitable thermal initiators can be used as radical starters in the temperature range from 70 to 150° C., preferably from 90 to 150° C. Preferred thermal initiators comprise at least one initiator selected from: Dilauroyl peroxide, di-tert.butyl peroxide, tert-butyl-peroxy-2-ethylhexanoate, dibenzoyl peroxide, dicumyl peroxide, dicumyl hydroperoxide, 2,2'-azobis-isobutyronitrile, benzylbarbituric acid derivative, particularly preferably tert-butyl-peroxy-2-ethylhexanoate, dibenzoyl peroxide, dicumyl peroxide, dicumyl hydroperoxide, azobis-isobutyronitrile, benzylbarbituric acid derivative, such as phenylbenzylbarbituric acid, cyclohexylbenyzlbarbituric acid.

The following initiators and/or initiator systems for auto- or cold polymerization comprise a) at least one initiator, in particular at least one peroxide and/or azo compound, in particular LPO: dilauroyl peroxide, BPO: dibenzoyl peroxide, t-BPEH: tert.-butylper-2-ethylhexanoate, AIBN: 2,2'-azobis-(isobutyronitrile), DTBP: di-tert.butyl peroxide, and optionally b) at least one activator, in particular at least one aromatic amine, such as N,N-dimethyl-p-toluidine, N,N-dihydroxyethyl-p-toluidine and/or p-dibenzylaminobenzoic acid diethyl ester or c) at least one initiator system selected from redox systems, in particular a combination selected from dibenzoyl peroxide, dilauroyl peroxide and camphorquinone with amines selected from N,N-dimethyl-p-toluidine, N-N-dihydroxyethyl-p-toluidine and p-dimethylaminobenzoic acid diethyl ester. Alternatively, the initiator system may be a redox system comprising a peroxide, and a reducing agent selected from ascorbic acid, ascorbic acid derivative, barbituric acid or a barbituric acid derivative, sulfinic acid, sulfinic acid derivative, particularly preferred is a redox system comprising (i) barbituric acid or thiobarbituric acid or a barbituric acid or thiobarbituric acid derivative and (ii) at least one copper salt or copper complex and (iii) at least one compound with an ionic halogen atom, particularly preferred is a redox system comprising 1-benzyl-5-phenylbarbituric acid, copper acetylacetonate and benzyldibutylammonium chloride. Particularly preferably, polymerization in the 2-component denture base material is started via a barbituric acid derivative.

In principle, initiators for the polymerization reaction of cold- or autopolymerizing starting mixtures are those with which free-radical polymerization reactions can be started. Preferred initiators are peroxides as well as azo compounds, such as the following: LPO: dilauroyl peroxide, BPO: dibenzoyl peroxide, t-BPEH: tert-butyl per-2-ethyl hexanoate, AIBN: 2,2'-azobis-(isobutyronitrile), DTBP: di-tert.-butyl peroxide.

In order to accelerate the initiation of radical polymerization by peroxides, suitable activators, e.g. aromatic amines, can be added. Examples of suitable amines are N,N-dimethyl-p-toluidine, N,N-dihydroxyethyl-p-toluidine and p-dibenzylamino-benzoic acid diethyl ester. Here, the amines regularly act as co-initiators and are usually present in an amount of up to 0.5 wt.-%.

The following embodiments are intended to illustrate the invention without limiting the invention to these examples.

EXAMPLES OF EMBODIMENTS

Methods

Preparation of the composite pastes: The monomers, reactive diluents, initiators, additives and fillers are weighed out and homogenized in a speed mixer (Hauschild-DAC 600.1 FVZ) at 1500 $min^{-1}$ for 5 min at normal pressure. The fillers are weighed in successively to the monomer mixture and the mixture is again homogenized in the speed mixer at 1500 $min^{-1}$ for 5 min at normal pressure. The composite is then homogenized again using a three roll mill. The composite is degassed again in the speed mixer at 700 $min^{-1}$ for 5 min under vacuum.

Determination of the flexural strength and the modulus of elasticity: The production of the flexural rods and the determination of the flexural strength and the modulus of elasticity (E-modulus/Young's modulus) are carried out according to DIN EN ISO 4049:2019, 7.11 on a test specimen with the dimensions 25+/−2 mm×2.0+/−0.1 mm×2.0+/−0.1 mm, the test specimens are stored in water at 37° C. until the start of the measurement (light source: Kulzer, Translux Wave, with blue light (emission maximum approx. 440 to 460 nm), 700 $mW/cm^2$, 20 s). 24 h after irradiation, the specimen is loaded with a crosshead speed of 0.75+/−0.25 mm/min or with a load increase of 50+/−16 N/min up to the yield point, or until fracture.

Determination of the depth of cure: The determination of the depth of cure/polymerization is performed according to DIN EN ISO 4049:2019, 7.10 (light source: Translux 2Wave, 1200 $mW/cm^2$, 20 s), specimen cylindrical greater than 6 mm in length, diameter 4 mm. If the polymerization depth is greater than 3 mm the specimen has been at least 2 mm longer than the polymerization depth indicated twice. The value of the polymerization depth given in this document is therefore equal to the absolute value of the polymerization depth divided by two.

Determination of transparency: Circular test specimens with a diameter of 20 mm and a thickness of 1 mm are produced from the composite paste by photopolymerization (light source: Kulzer, Translux Wave, 700 $mW/cm^2$). Colorimetric measurement of the test specimens is carried out using the Datacolor SF 800 device, with transparency of the test specimens against a black background.

Determination of polymerization shrinkage according to Watts or Bonded Disk method: The composite is applied to a slide glass between a 1 mm high spacer ring and covered with the aid of a coverslip. The material sample wets the underside of the coverslip. The material sample is then irradiated from the underside with the aid of a light source (Kulzer Translux 2Wave, 1200 $mW/cm^2$, 20 s) and the deflection of the coverslip is determined from the top side with the aid of a laser (Lit. Determination of polymerization shrinkage kinetics in visible-light-cured materials: methods development; D.C. Watts et al, Dental Materials, October 1991, 281 ff).

Determination of the double bond conversion U: The double bond conversion U is determined using ATR-IR. In this method, a sample of material is applied to a cylindrical mold 2 mm deep. The composite-filled cylindrical mold is placed on top of an ATR crystal, which is now located on the underside of the material sample. An IR spectrum (wavelength range: 4000 $cm^{-1}$-700 $cm^{-1}$) is recorded. The composite is then covered on the upper side with a transparent film, irradiated with the aid of a light source (light source: Translux 2Wave, 1200 $mW/cm^2$, 20 s) and another IR spectrum is recorded 10 min after photopolymerization has ended. The quotient of the integral of the —C═C— double bond signal (~1645 $cm^{-1}$) before and after photopolymerization gives the residual double bond content, from which the double bond conversion U in % is determined.

$$U = 100 - \left(\frac{\text{total area } unpolym.}{\text{total area } polym.} \cdot 100\right)$$

Method Determination of particle sizes: A determination of particle sizes can be made using established test methods preferably laser diffraction (DLS), SOP, MALVERN Mastersizer 2000. Other methods familiar to the skilled person are defined in the standards ISO 22412:2017 Particle Size Analysis-Dynamic Light Scattering (DLS) or ISO 13320: 2020 Particle Size Analysis-Laser Diffraction Methods. In addition, particle size determination can be performed batchwise using DLS with Zeta Sizer Advanced Range (0.3 nm to 15 microns) instruments or as a continuous in-process control using Zetasizer AT (0.3 nm to 10 microns) from Malvernpananalytical. According to these methods, $D_{10}$, $D_{50}$, $D_{90}$ can also be determined.

Viscosity: Viscosity is preferably measured according to DIN 1342-2;2003-11 newtonian liquids or DIN 1342-3; 2003-11 non newtonian liquids with a rheometer (Anton Par, Physicist NCR 301, viscosity ranges 200-3000 m·Pas at 100/s 23° C.).

EXAMPLES

Designation in the Following Examples

| Designation | Component |
|---|---|
| Crosslinker VG | Monomer: Bis-GMA |
| Crosslinker according to the invention | (ii) Monomers/Mixture: Monomer blend of urethane of formula I, monomer No. 1 |

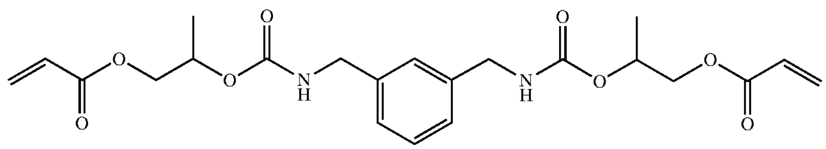

and thiolurethane, in particular of the formula V

-continued

| Designation | Component |
|---|---|
| | 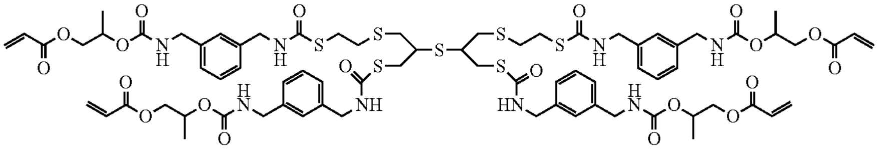 |
| | Formula V, Monomer No. 2 |
| Diluent | (ii) Monomers: TEGDMA (reference) or TCDDMDA, TCDDMDMA, monomer with ether, thioether or tri-functional triester, thioethers used: 4, 6, 7, 9. |
| Fluorescent agent | Diethyl(2,5-dihydroxyterephthalate): |
| UV filter | 2-Hydroxy-4-methoxybenzophenone |
| Photo initiator | Camphorquinone |
| Photo initiator | 1-Phenyl-1,2-propanedione |
| Coinitiator | 2-Ethylhexyl-4-dimethylaminobenzoate |
| Stabilizer/Antioxidant | 2,6-Di-tert-butyl-4-methylphenol |
| Filler | Ytterbium trifluoride, dental glass 1.5 μm (silanized): Filler (surface functionalized) |

VG: Comparison example

For the present invention disclosure, the following dental composites were prepared and cured by photoinitiation (light source: Translux Wave (Kulzer), 1000 mW/cm$^2$, 20 s):

TABLE 1a

Composite formulations with a filler content of 68 wt.-% in the total composition.

| Material designation | Share [wt.-%] | Ratio crosslinker/diluent |
|---|---|---|
| Crosslinker | 31.24 | 101/1 |
| diluent | 0.31 | |
| diethyl(2,5-dihydroxyterephthalate) | 0.01 | |
| 2-hydroxy-4-methoxybenzophenone | 0.22 | |
| camphorquinone | 0.04 | |
| 1-Phenyl-1,2-propanedione | 0.02 | |
| 2,6-di-tert-butyl-4-methylphenol | 0.03 | |
| 2-ethylhexyl-4-dimethylaminobenzoate | 0.14 | |
| ytterbium trifluoride | 15 | |
| dental glass 1.5 μm (silanized) | 53 | |

TABLE 1b

Composite formulations with a filler content of 68 wt.-% in the Overall composition.

| | | |
|---|---|---|
| crosslinker | 28.39 | 9/1 |
| diluent | 3.15 | |
| diethyl(2,5-dihydroxyterephthalate) | 0.01 | |
| 2-hydroxy-4-methoxybenzophenone | 0.22 | |
| camphorquinone | 0.04 | |
| 1-phenyl-1,2-propanedione | 0.02 | |
| 2,6-di-tert-butyl-4-methylphenol | 0.03 | |
| 2-ethylhexyl-4-dimethylaminobenzoate | 0.14 | |
| ytterbium trifluoride | 15 | |
| dental glass 1.5 μm (silanized) | 53 | |

TABLE 1c

Composite formulations with a filler content of 68 wt.-% in the total composition.

| | | |
|---|---|---|
| crosslinker | 26.29 | 5/1 |
| diluent | 5.26 | |
| diethyl(2,5-dihydroxyterephthalate) | 0.01 | |
| 2-hydroxy-4-methoxybenzophenone | 0.22 | |
| camphorquinone | 0.04 | |
| 1-phenyl-1,2-propanedione | 0.02 | |
| 2,6-di-tert-butyl-4-methylphenol | 0.03 | |
| 2-ethylhexyl-4-dimethylaminobenzoate | 0.14 | |
| ytterbium trifluoride | 15 | |
| dental glass 1.5 μm (silanized) | 53 | |

TABLE 1d

Composite formulations with a filler content of 68 wt.-% in the total composition.

| | | |
|---|---|---|
| crosslinker | 21.03 | 2/1 |
| diluent | 10.52 | |
| diethyl(2,5-dihydroxyterephthalate) | 0.01 | |
| 2-hydroxy-4-methoxybenzophenone | 0.22 | |
| camphorquinone | 0.04 | |
| 1-phenyl-1,2-propanedione | 0.02 | |
| 2,6-di-tert-butyl-4-methylphenol | 0.03 | |
| 2-ethylhexyl-4-dimethylaminobenzoate | 0.14 | |
| ytterbium trifluoride | 15 | |
| dental glass 1.5 μm (silanized) | 53 | |

TABLE 2

Composite formulations with varying filler contents from 30 to 75 wt.-% in the total composition.

| Material designation | Share [wt.-%] | Ratio crosslinker/ diluent | Filler content [wt.-%] |
|---|---|---|---|
| crosslinker: Monomer blend 1 + 2 | 57.51 | 5/1 | 30 |
| diluent: TEGDMA | 11.50 | | |
| diethyl(2,5-dihydroxyterephthalate) | 0.02 | | |
| 2-hydroxy-4-methoxybenzophenone | 0.48 | | |
| camphorquinone | 0.08 | | |
| 1-Phenyl-1,2-propanedione | 0.04 | | |
| 2,6-di-tert-butyl-4-methylphenol | 0.06 | | |
| 2-ethylhexyl-4-dimethylaminobenzoate | 0.31 | | |
| ytterbium trifluoride | 6.62 | | |
| dental glass 1.5 μm (silanized) | 23.38 | | |
| crosslinker: Monomer blend 1 + 2 | 20.54 | 5/1 | 75 |
| diluent: TEGDMA | 4.11 | | |
| diethyl (2,5-dihydroxyterephthalate) | 0.01 | | |

TABLE 2-continued

| Composite formulations with varying filler contents from 30 to 75 wt.-% in the total composition. | | | |
|---|---|---|---|
| Material designation | Share [wt.-%] | Ratio crosslinker/ diluent | Filler content [wt.-%] |
| 2-hydroxy-4-methoxybenzophenone | 0.17 | | |
| camphorquinone | 0.03 | | |
| 1-phenyl-1,2-propanedione | 0.01 | | |
| 2,6-di-tert-butyl-4-methylphenol | 0.02 | | |
| 2-ethylhexyl-4-dimethylaminobenzoate | 0.11 | | |
| ytterbium trifluoride | 16.54 | | |
| dental glass 1.5 μm (silanized) | 58.46 | | |

TABLE 3a

| Compositions - crosslinkers with different filler contents. | | | | | | |
|---|---|---|---|---|---|---|
| | Crosslinker | Diluent | Solids content [wt.-%] | Share of crosslinker [wt.-%] | Proportion of diluent [wt.-%] | Ratio crosslinker/ diluent |
| VG | BisGMA | TEGDMA | 68 | 26.32 | 5.25 | 5 |
| Ex. F1 | Monomer blend No. 1 + No. 2 | TEGDMA | 68 | 26.29 | 5.29 | 5 |
| Ex. F2 | Monomer blend No. 1 + No. 2 | TEGDMA | 30 | 57.51 | 11.5 | 5 |
| Ex. F3 | Monomer blend No. 1 + No. 2 | TEGDMA | 75 | 20.54 | 4.11 | 5 |

TABLE 3b

| Properties of crosslinkers with different filler contents. | | | | | | |
|---|---|---|---|---|---|---|
| | Flexural strength [MPa] | E-modulus [MPa] | Curing-deep (ISO4049) [mm] | Trans-parency [%] | Shrink-age (WATTS) [%] | Double-BINDING sales [%] |
| VG | 111 | 6134 | 6 | 52.72 | 3.04 | 46.41 |
| Ex. F1 | 113 | 6323 | 4.5 | 77.32 | 2.31 | 49.86 |
| Ex. F2 | 74 | 2101 | 6.1 | 83.91 | 3.41 | 49.36 |
| Ex. F3 | 119 | 7724 | 5.5 | 75.23 | 2.49 | 54.12 |

TABLE 4a

| Comparative examples VG1 to VG5 with crosslinker: Bis-GMA | | | | | | | |
|---|---|---|---|---|---|---|---|
| No. | Crosslinker | Diluent | Solids content [wt.-%] | Crosslinker/ diluent [wt.-%/ wt.-%] | Flexural strength [MPa] | Module [MPa] | Module/ Bending strength |
| VG1 | BisGMA | TEGDMA | 68 | 101 | 69 | 3668 | 53.16 |
| VG2 | BisGMA | TEGDMA | 68 | 9 | 106 | 6898 | 61.44 |
| VG4 | BisGMA | TEGDMA | 68 | 5 | 121 | 7134 | 55.26 |
| VG5 | BisGMA | TEGDMA | 68 | 2 | 91 | 5293 | 58.16 |

TABLE 4b

| Comparative examples VG1 to VG5 | | | | | | |
|---|---|---|---|---|---|---|
| No. | Crosslinker | Diluent | Curing-Depth (ISO4049) [mm] | Transparency [%] | Shrink [%] | Double-bond sales [%] |
| VG1 | BisGMA | TEGDMA | 3.80 | 51.01 | 1.61 | 18.31 |
| VG2 | BisGMA | TEGDMA | 5.63 | 51.18 | 2.62 | 41.02 |
| VG4 | BisGMA | TEGDMA | 6.00 | 52.72 | 3.04 | 46.41 |
| VG5 | BisGMA | TEGDMA | 6.00 | 70.99 | 3.44 | 49.02 |

TABLE 5a

| Examples according to the invention with monomers No. 1 and No. 2 as crosslinkers | | | | | | | |
|---|---|---|---|---|---|---|---|
| No. | Crosslinker | Diluent | Solids content [wt.-%] | Crosslinker/ diluent [wt.-%/ wt.-%] | flexural strength [MPa] | Module [MPa] | Module/ Bending strength |
| 1 | 1 + 2 | TEGDMA | 68 | 101 | 118 | 7009 | 59.40 |
| 2 | 1 + 2 | TEGDMA | 68 | 9 | 116 | 6609 | 56.97 |
| 3 | 1 + 2 | TEGDMA | 68 | 5 | 113 | 6323 | 55.96 |
| 4 | 1 + 2 | TEGDMA | 68 | 2 | 105 | 6084 | 57.94 |
| 5 | 1 + 2 | TEGDMA | 30 | 5 | 74 | 2101 | 28.39 |
| 6 | 1 + 2 | TEGDMA | 75 | 5 | 119 | 7724 | 64.91 |
| 7 | 1 + 2 | 6 | 68 | 101 | 103 | 5679 | 55.14 |
| 8 | 1 + 2 | 6 | 68 | 9 | 118 | 6738 | 57.10 |
| 9 | 1 + 2 | 6 | 68 | 5 | 128 | 6583 | 51.43 |
| 10 | 1 + 2 | 6 | 68 | 2 | 100 | 4684 | 46.84 |
| 11 | 1 + 2 | TCDDMDA | 68 | 101 | 105 | 5606 | 53.39 |
| 12 | 1 + 2 | TCDDMDA | 68 | 9 | 111 | 6106 | 55.01 |
| 13 | 1 + 2 | TCDDMDA | 68 | 5 | 109 | 6181 | 56.71 |
| 14 | 1 + 2 | TCDDMDA | 68 | 2 | 100 | 5264 | 52.64 |
| 15 | 1 + 2 | TCDDMDMA | 68 | 101 | 109 | 6203 | 56.91 |
| 16 | 1 + 2 | TCDDMDMA | 68 | 9 | 115 | 6407 | 55.71 |
| 17 | 1 + 2 | TCDDMDMA | 68 | 5 | 100 | 5842 | 58.42 |
| 18 | 1 + 2 | TCDDMDMA | 68 | 2 | 95 | 5776 | 60.80 |
| 19 | 1 + 2 | 4 | 68 | 101 | 93 | 4709 | 50.63 |
| 20 | 1 + 2 | 4 | 68 | 9 | 101 | 4989 | 49.40 |
| 21 | 1 + 2 | 4 | 68 | 5 | 99 | 4930 | 49.80 |
| 22 | 1 + 2 | 4 | 68 | 2 | 96 | 4605 | 47.97 |
| 23 | 1 + 2 | 7 | 68 | 101 | 104 | 5320 | 51.15 |
| 24 | 1 + 2 | 7 | 68 | 9 | 95 | 4998 | 52.61 |
| 25 | 1 + 2 | 7 | 68 | 5 | 104 | 5320 | 51.15 |
| 26 | 1 + 2 | 7 | 68 | 2 | 103 | 5194 | 50.43 |
| 27 | 1 + 2 | 9 | 68 | 101 | 99 | 5055 | 51.06 |
| 28 | 1 + 2 | 9 | 68 | 9 | 88 | 4124 | 46.86 |
| 29 | 1 + 2 | 9 | 68 | 5 | 96 | 4175 | 43.49 |
| 30 | 1 + 2 | 9 | 68 | 2 | 89 | 3725 | 41.85 |

TABLE 5b

| Examples according to the invention | | | | | | |
|---|---|---|---|---|---|---|
| No. | Crosslinker | Diluent | Depth of cure (ISO4049) [mm] | Transparency [%] | Shrinkage [%] | Double-bond sales [%] |
| 1 | 1 + 2 | TEGDMA | 5.39 | 73.86 | 1.75 | 43.39 |
| 2 | 1 + 2 | TEGDMA | 5.50 | 78.65 | 2.78 | 55.09 |
| 3 | 1 + 2 | TEGDMA | 4.45 | 77.32 | 2.31 | 49.86 |
| 4 | 1 + 2 | TEGDMA | 4.85 | 79.57 | 3.71 | 62.3 |
| 5 | 1 + 2 | TEGDMA | 6.10 | 83.91 | 3.41 | 49.36 |
| 6 | 1 + 2 | TEGDMA | 5.45 | 75.23 | 2.49 | 54.12 |
| 7 | 1 + 2 | 6 | 4.40 | 70.3 | 1.72 | 42.22 |
| 8 | 1 + 2 | 6 | 6.25 | 70.27 | 2.53 | 53.49 |
| 9 | 1 + 2 | 6 | 6.00 | 74.01 | 2.79 | 59.48 |
| 10 | 1 + 2 | 6 | 6.00 | 79.61 | 2.96 | 63.24 |
| 11 | 1 + 2 | TCDDMDA | 5.30 | 71.94 | 1.67 | 43.87 |
| 12 | 1 + 2 | TCDDMDA | 5.60 | 74.57 | 2.04 | 46.84 |

TABLE 5b-continued

| Examples according to the invention | | | | | | |
|---|---|---|---|---|---|---|
| No. | Crosslinker | Diluent | Depth of cure (ISO4049) [mm] | Transparency [%] | Shrinkage [%] | Double-bond sales [%] |
| 13 | 1 + 2 | TCDDMDA | 4.95 | 74.35 | 2.23 | 47.57 |
| 14 | 1 + 2 | TCDDMDA | 5.30 | 76.38 | 2.66 | 52.3 |
| 15 | 1 + 2 | TCDDMDMA | 4.90 | 70.53 | 1.84 | 44.86 |
| 16 | 1 + 2 | TCDDMDMA | 4.90 | 74.36 | 2.12 | 44.61 |
| 17 | 1 + 2 | TCDDMDMA | 4.95 | 74.57 | 2.24 | 45.17 |
| 18 | 1 + 2 | TCDDMDMA | 5.35 | 77.7 | 2.72 | 44.37 |
| 19 | 1 + 2 | 4 | 4.70 | 71.05 | 1.64 | 44.77 |
| 20 | 1 + 2 | 4 | 4.85 | 77.49 | 2.15 | 46.16 |
| 21 | 1 + 2 | 4 | 4.20 | 79.43 | 2.43 | 46.06 |
| 22 | 1 + 2 | 4 | 4.55 | 78.56 | 2.88 | 50.89 |
| 23 | 1 + 2 | 7 | 4.95 | 72.78 | 1.68 | 48.4 |
| 24 | 1 + 2 | 7 | 4.35 | 76.74 | 2.08 | 48.3 |
| 25 | 1 + 2 | 7 | 3.45 | 79.41 | 2.43 | 50.6 |
| 26 | 1 + 2 | 7 | 4.80 | 79.63 | 3.03 | 52.4 |
| 27 | 1 + 2 | 9 | 4.70 | 77.78 | 1.73 | 44.49 |
| 28 | 1 + 2 | 9 | 4.85 | 76.79 | 2.1 | 47.43 |
| 29 | 1 + 2 | 9 | 5.00 | 71.87 | 2.45 | 52.04 |
| 30 | 1 + 2 | 9 | 4.70 | 79.21 | 3.14 | 61.38 |

TABLE 6

| VG 1 to 5, examples 6 to 10 with diluent 6 | | | | | | | | | |
|---|---|---|---|---|---|---|---|---|---|
| No. | Crosslinker | Diluent | Solid content [wt.-%] | Crosslinker [wt.-%] | Diluent [wt %] | Ratio Crosslinker/ diluent | Flexural strength [MPa] | E-modulus [MPa] | Curing depth (ISO4049) [mm] |
| VG1 | BisGMA | TEGDMA | 68 | 31.24 | 0.31 | 101 | 69 | 3668 | 3.80 |
| VG2 | BisGMA | TEGDMA | 68 | 28.42 | 3.16 | 9 | 106 | 6898 | 5.63 |
| VG4 | BisGMA | TEGDMA | 68 | 26.32 | 5.25 | 5 | 121 | 7134 | 6.18 |
| VG5 | BisGMA | TEGDMA | 68 | 21.03 | 10.52 | 2 | 91 | 5293 | 6.20 |
| 7 | 1 + 2 | 6 | 68 | 31.24 | 0.31 | 101 | 103 | 5679 | 4.40 |
| 8 | 1 + 2 | 6 | 68 | 28.38 | 3.16 | 9 | 118 | 6738 | 6.25 |
| 9 | 1 + 2 | 6 | 68 | 26.01 | 5.21 | 5 | 128 | 6583 | 6.00 |
| 10 | 1 + 2 | 6 | 68 | 21.03 | 10.52 | 2 | 100 | 4684 | 6.00 |

TABLE 7

| VG 1 to 5, examples crosslinker 1 + 2 and diluent TEGDMA | | | | | | | | |
|---|---|---|---|---|---|---|---|---|
| No. | Crosslinker | Diluent | Solids- [wt.-%] | Crosslinker [wt.-%] | Diluent [wt.-%] | Transparency [%] | Shrinkage (WATTS) [%] | Double-BINDING sales [%] |
| VG1 | BisGMA | TEGDMA | 68 | 31.24 | 0.31 | 51.01 | 1.61 | 18.31 |
| VG2 | BisGMA | TEGDMA | 68 | 28.42 | 3.16 | 51.18 | 2.62 | 41.02 |
| VG4 | BisGMA | TEGDMA | 68 | 26.32 | 5.25 | 52.72 | 3.04 | 46.41 |
| VG5 | BisGMA | TEGDMA | 68 | 21.03 | 10.52 | 70.99 | 3.44 | 49.02 |
| 1 | 1 + 2 | TEGDMA | 68 | 31.24 | 0.31 | 73.86 | 1.75 | 43.39 |
| 2 | 1 + 2 | TEGDMA | 68 | 28.4 | 3.15 | 78.65 | 2.78 | 55.09 |
| 3 | 1 + 2 | TEGDMA | 68 | 26.29 | 5.29 | 77.32 | 2.31 | 49.86 |
| 4 | 1 + 2 | TEGDMA | 68 | 21.03 | 10.52 | 79.57 | 3.71 | 62.3 |

The invention claimed is:

1. A polymerizable composition comprising
(i) 0.01 to 90 wt.-% of at least one inorganic filler component,
(ii) 5 to 99.97 wt.-% comprising at least two urethane acrylates, wherein one urethane acrylate is at least one urethane acrylate of formula I having a divalent hydrocarbon group

I

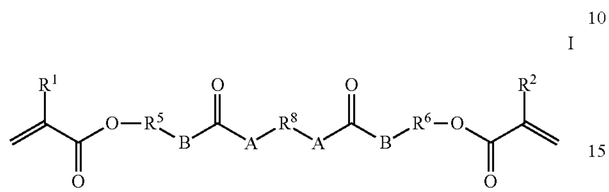

with A=O, if B═NH or A=NH, if B═O,
$R^1$═H or $CH_3$, $R^2$═H or $CH_3$,
$R^5$ and $R^6$ are each independently selected from linear C2 to C6 alkylene groups or linear C2 to C6 oxyalkylene groups, wherein $R^5$ and $R^6$ are optionally each independently have a C1-C3 alkyl group or (meth)acryloxymethylene group, and
$R^8$ is a divalent hydrocarbon group having 6 to 12 carbon atoms, and the second urethane acrylate comprises at least one bifunctional thiolurethane group and at least one olefinic group, wherein
the second urethane acrylate having a structure of the general formula V,

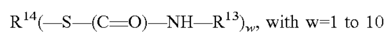

$R^{14}(—S—(C═O)—NH—R^{13})_w$, with w=1 to 10

V wherein residue $R^{13}$ is a residue each independently selected from residues having at least one olefinic group, and $R^{14}$ having one of the following structures of the formulas VIa to VIg VIa

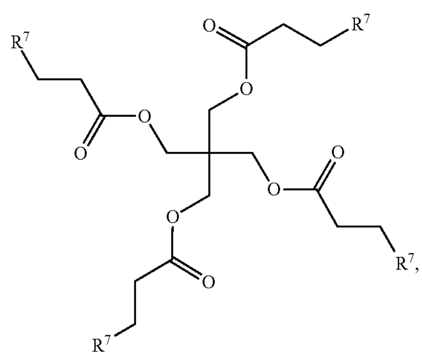

VIb

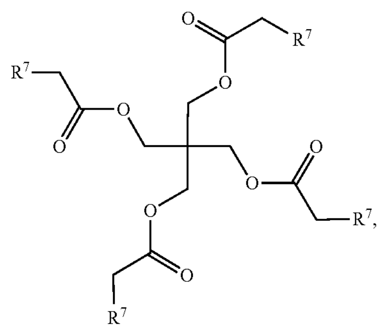

-continued

VIc

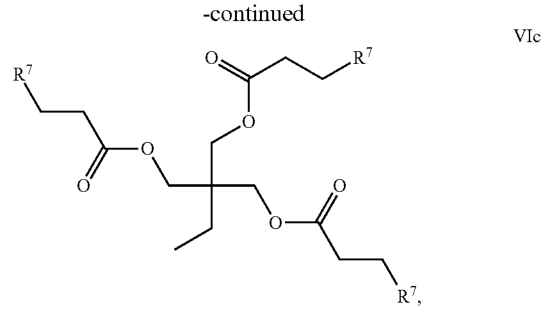

VId

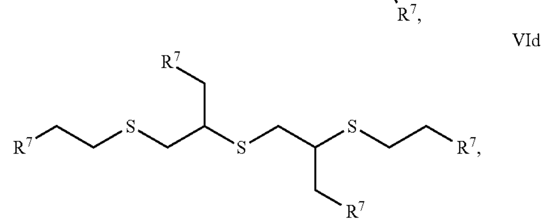

VIe

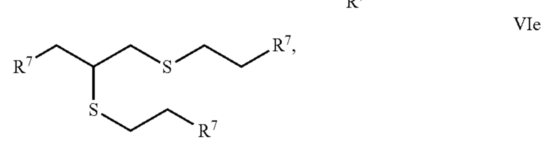

VIf

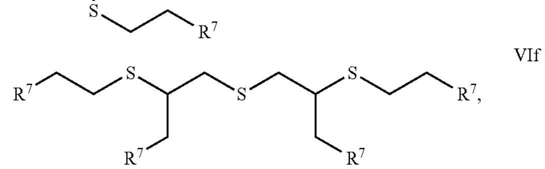

VIg

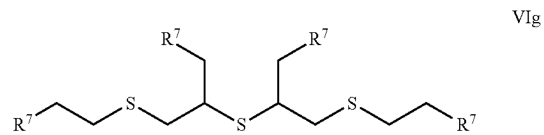

with $R^7$ in formula VIa to VIg each independently selected from

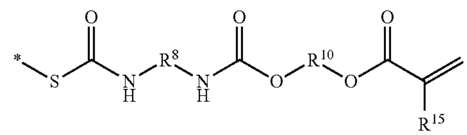

with $R^8$ each independently being a divalent hydrocarbon group having 6 to 12 C-atoms, with $R^{10}$ each independently selected from linear C2 to C6 alkylene groups or linear C2 to C6 oxyalkylene groups, wherein $R^{10}$ optionally each independently having a C1-C3 alkyl group or (meth)acryloxymethylene group and with $R^{15}$ each independently having H or C1 to C4 alkyl, and/or mixtures of urethane acrylates comprising these,
(iii) 0.01 to 25 wt.-% comprising at least one di-, tri-, tetra- or multi-functional monomer having at least one ether group, thioether group, an at least at least tri-functional triester and/or a di-functional diester, wherein the diester is selected from tricyclodecane dimethanol dimethacrylate and tricyclodecane dimethanol diacrylate, or mixtures comprising at least two of these di-, tri-, tetra- or multi-functional monomers,
(iv) 0.01 to 10 wt.-% of at least one initiator, an initiator system, optionally at least one stabilizer and optionally at least one pigment and optionally further additives, wherein the total composition of the polymerizable composition amounts up to 100 wt.-%.

2. Polymerizable composition according to claim 1, wherein the formula V has, as $R^{10}$ each independently having a C1-C3 alkyl group or (meth)acryloxymethylene group.

3. Polymerizable composition according to claim 1, wherein the urethane acrylate of the general formula I and/or of the formula V is in each case independently with $R^8$ and/or comprises bivalent aromatic hydrocarbon having 6 to 12 carbon atoms, divalent alicyclic hydrocarbon having 6 to 12 carbon atoms or divalent linear or branched alkylene having 6 to 12 carbon atoms or divalent linear or branched alkylene having an aromatic or alicyclic group.

4. Polymerizable composition according to claim 1, wherein it comprises at least one urethane acrylate of the general formula I

I

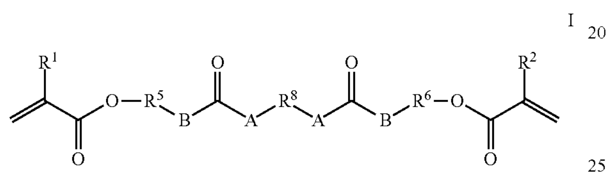

with A=O when B=NH or A=NH when B=O and with $R^1$=H or $CH_3$, $R^2$=H or $CH_3$, and $R^5$ and $R^6$ are each independently selected from linear C2 to C6 alkylene groups or linear C2 to C6 oxyalkylene groups, wherein $R^5$ and $R^6$ each optionally have independently a C1-C3 alkyl group or (meth)acryloxymethylene group, and $R^8$ comprises one of the following divalent groups

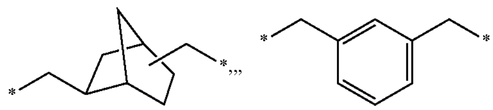

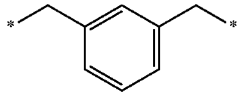

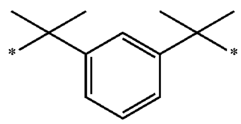

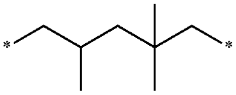

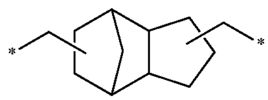

5. Polymerizable composition according to claim 1, wherein it comprises (iii) at least one di-, tri-, tetra- or multi-functional monomer having at least an ether group of the formula III, thioether group of the formula IV and/or an at least tri- or tetra-functional triester of the formula II or mixtures at least two of the monomers, in particular comprising at least one monomer of the formulas IIa, IIb, IIc, III, IVa, IVb, IVc, IVd or mixtures comprising at least two of the monomers, IIa

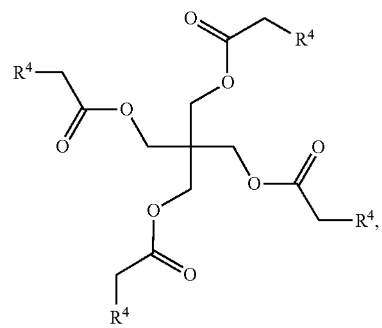

IIb

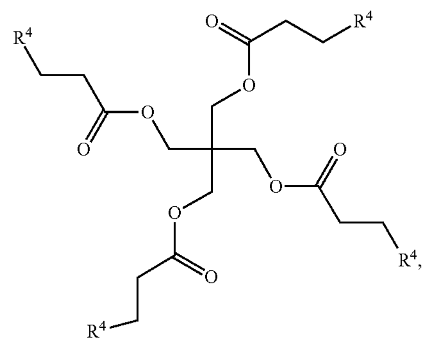

IIc

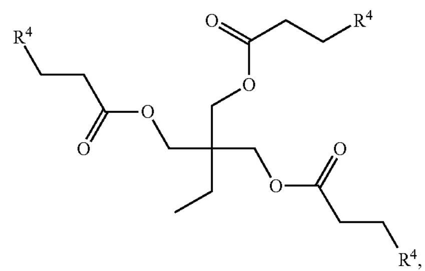

III

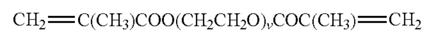

$CH_2{=}C(CH_3)COO(CH_2CH_2O)_vCOC(CH_3){=}CH_2$ with v = 30 to 20, v = 3 to 15, v = 3 to 8

IVa

IVb

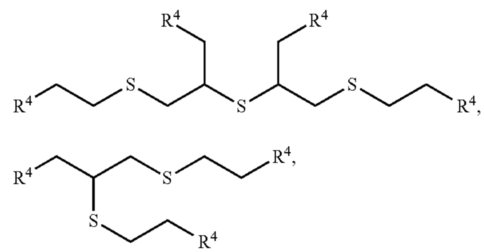

IVc

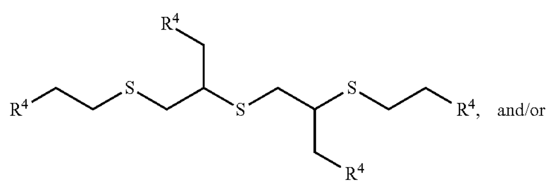

and/or

IVd

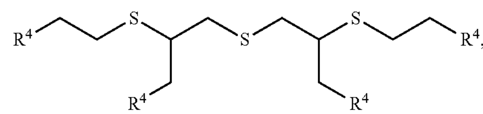

with in each case independently $R^4$=

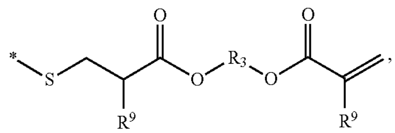

wherein in each case independently $R^9$=H or $CH_3$, and with $R^3$=

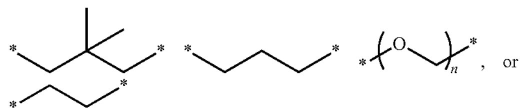

n=1 to 8.

6. Polymerizable composition according to claim 1, wherein it comprises (i) 5 to 90 wt.-% of an inorganic filler component comprising at least one glass, silicate, metal oxide, mixed oxide, silicon dioxide, zirconium dioxide, zinc oxide and/or mixtures of at least two of said components, said components having an average particle size of 0.2 μm to 10 μm, and optionally at least one amorphous metal oxide with an average primary particle size of 10 nm to 115 nm, and (ii) 10 to 85 wt.-% of at least two urethane acrylates, wherein the urethane acrylates comprise at least one urethane acrylate of the formula I and at least one second urethane acrylate having at least one bifunctional thiolurethane group and at least one olefinic group, (iii) 0.01 to 25 wt.-% of at least one di-, tri-, tetra- or multi-functional monomer having at least one ether group, thioether group and/or a at least a tri-functional triester and/or a di-functional diester, wherein the diester is selected from tricyclodecane dimethanol dimethacrylate and tricyclodecane dimethanol diacrylate or mixtures of at least two of these di-, tri-, tetra- or multi-functional monomers, (iv) 0.01 to 10 wt.-% of at least one initiator, of an initiator system, and optionally at least one stabilizer and optionally at least one pigment, wherein the total composition of the composition amounts up to 100 wt.-%.

7. Polymerizable composition according to claim 1, wherein it comprises (i) 40 to 90 wt.-% of an inorganic filler component comprising at least one glass, silicate, quartz, feldspar, metal oxide, mixed oxide, silicon dioxide, zirconium dioxide and/or zinc oxide having an average particle size of 0.4 μm to 10 μm, and optionally at least one amorphous metal oxide having a mean primary particle size of 10 nm to 115 nm, and (ii) 10 to 59.98 wt.-% of at least two urethane acrylates, wherein the urethane acrylates comprise at least one urethane acrylate of formula I and at least one second urethane acrylate having at least one bifunctional thiolurethane group and at least one olefinic group, (iii) 0.01 to 15 wt.-% of at least one di-, tri-, tetra- or multi-functional monomer having at least one ether group, thioether group and/or an at least at least tri-functional triester and/or a di-functional diester, wherein the diester is selected from tricyclodecane dimethanol dimethacrylate and tricyclodecane dimethanol diacrylate or mixtures of these di-, tri-, tetra- or multi-functional monomers, (iv) 0.01 to 10 wt.-% of at least one initiator, of an initiator system, and optionally at least one stabilizer and optionally at least one pigment, wherein the total composition of the composition amounts up to 100 wt.-%.

8. Polymerizable composition according to claim 1, wherein it comprises as urethane acrylate of the formula I, at least one compound of the formula Ic to Io and/or mixtures thereof and optionally mixtures of isomers thereof, Ic

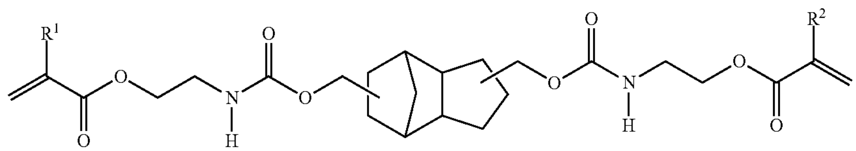

Id

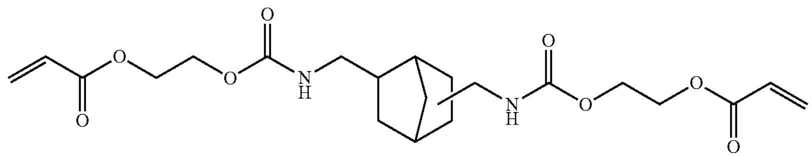

Ie

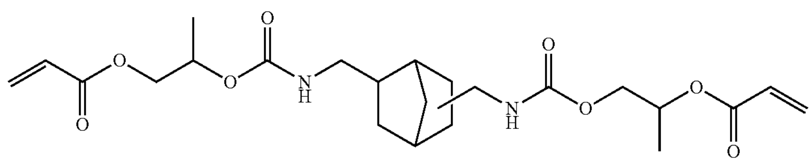

-continued
If
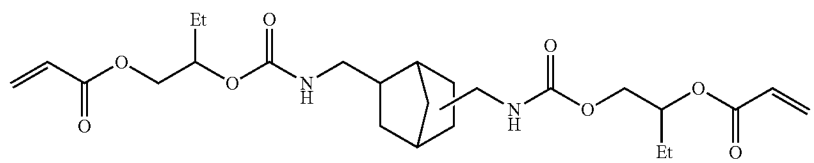
Ig
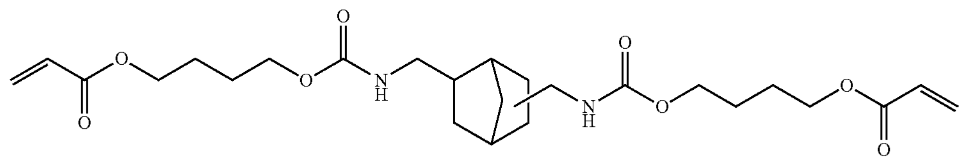
Ih
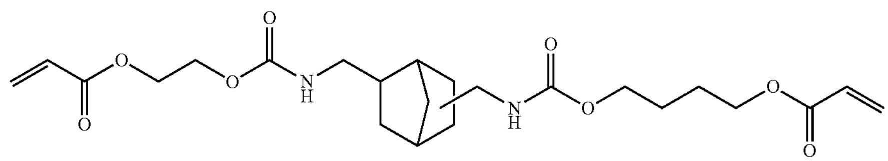
Ii
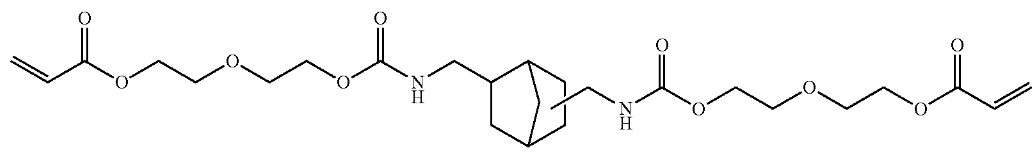
Ij
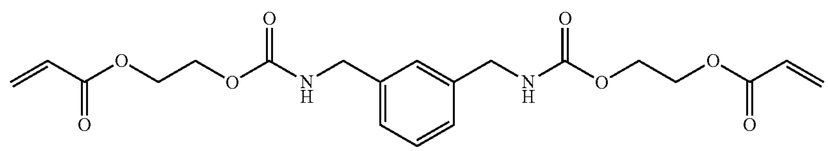
Ik
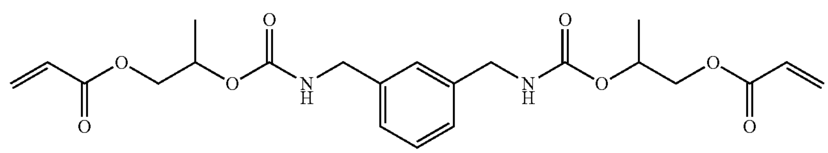 [SMILES: C=CC(=O)OCC(C)OC(=O)NCc1cccc(CNC(=O)OC(C)COC(=O)C=C)c1]
IL
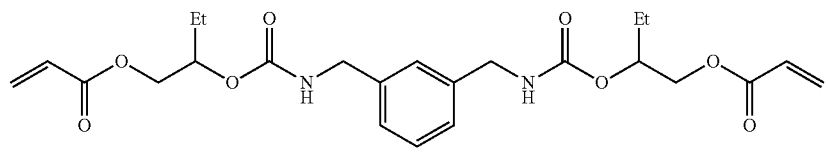
In
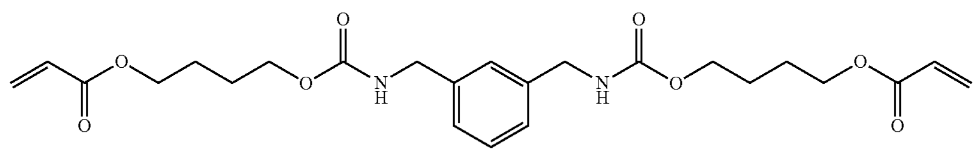
Im
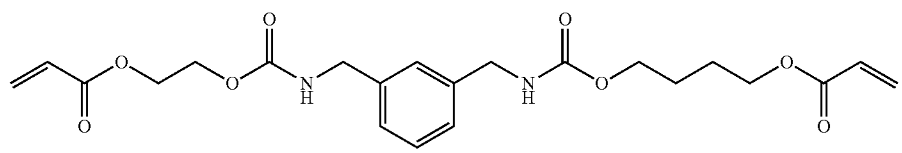
Io
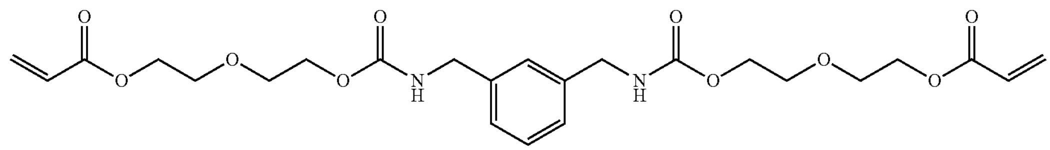
.

9. Polymerizable composition according to claim 1, wherein it comprises as (i) inorganic filler component (i.1) 0.005 to 85 wt.-% of at least one glass, silicate, quartz, feldspar, metal oxide mixed oxide, silica, zirconia, or a mixture comprising at least two of these filler components, and optionally (i.2) 0.005 to 5 wt.-% of amorphous metal oxide, in particular fumed silica and/or precipitated silicon dioxide, with respect to the total composition of the composition amounts up to 100 wt.-%.

10. Polymerizable composition according to claim 1, wherein it comprises at least two urethane acrylates comprising at least one urethane acrylate of formula I and at least one second urethane acrylate having at least one bifunctional thiolurethane group and at least one olefinic group in a mass ratio of from 1:1 to 100:1.

11. A polymerized composition comprising 0.01 to 90 wt.-% of at least one inorganic filler component, 5 to 99.98 wt.-% of at least one polymer based on the polymerization of at least monomers and/or prepolymers and mixtures thereof comprehensive at least two urethane acrylates, at least one urethane acrylate being of the formula I with a divalent hydrocarbon group is

I

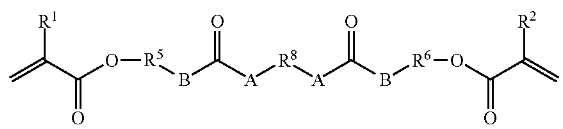

with A=O when B═NH or A=NH when B═O and with $R^1$═H or $CH_3$, $R^2$═H or $CH_3$, $R^5$ and $R^6$ are each independently selected from linear C2 to C6 alkylene groups or linear C2 to C6 oxyalkylene groups, wherein $R^5$ and $R^6$ optionally each independently have a C1-C3 alkyl group or (meth)acryloxymethylene group, preferably $CH_3$ and $R^8$ is a divalent hydrocarbon group having 6 to 12 carbon atoms, and the second urethane acrylate has at least one bifunctional thiolurethane group, and at least one olefinic group, wherein the second urethane acrylate having a structure of the general formula V,

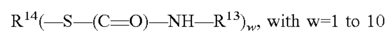

$R^{14}(—S—(C═O)—NH—R^{13})_w$, with w=1 to 10

V wherein residue $R^{13}$ is a residue each independently selected from residues having at least one olefinic group, and $R^{14}$ having one of the following structures of the formulas VIa to VIg VIa

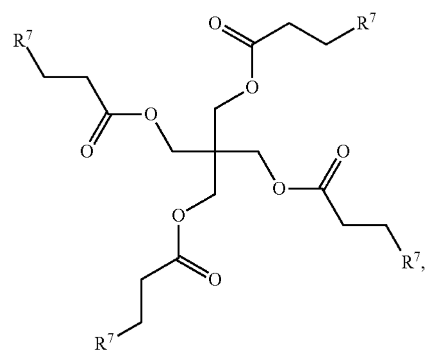

VIb

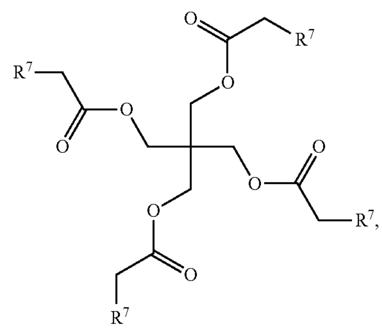

VIc

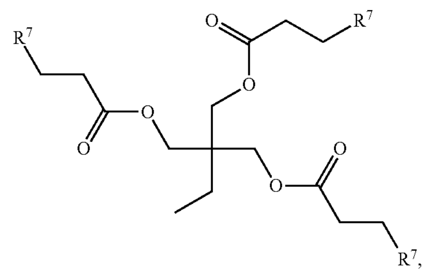

VId

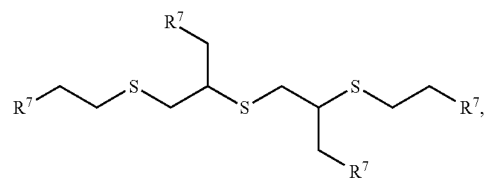

VIe

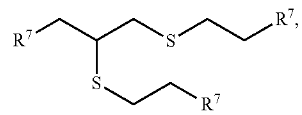

VIf

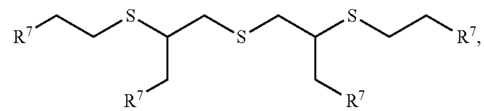

VIg

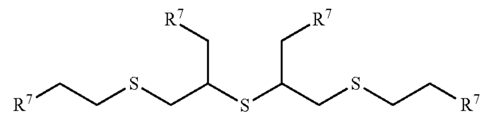

with $R^7$ in formula VIa to VIg each independently selected from

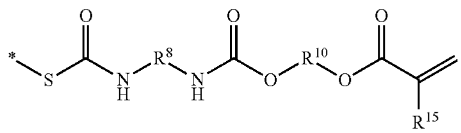

with $R^8$ each independently represents a divalent hydrocarbon group having 6 to 12 C-atoms, with $R^{10}$ each independently selected from linear C2 to C6 alkylene groups or linear C2 to C6 oxyalkylene groups, and with $R^{15}$ each independently having H or C1 to C4 alkyl, and/or mixtures of urethane acrylates comprising these, and/or mixtures of urethane acrylates comprising these, and at least one di-, tri-, tetra- or multi-functional monomer having at least an ether group, a thioether group, an at least tri-functional triester and/or a di-functional diester, the diester being selected from diester is selected from tricyclodecane dimethanol dimethacrylate and tricyclodecane dimethanol diacrylate or mixtures of at least two of the di-, tri-, tetra- or multi-functional monomers, and 0 to 10 wt.-% of at least one pigment, wherein the total composition of the polymerized composition amounts up to 100 wt.-%.

12. Polymerized composition according to claim 10, wherein the polymerized composition is present in the form of a material block, in particular the material block is present as a three-dimensional geometric shaped body, in particular as a milled blank without adapter or as a milled blank with adapter for fixing in an automated material-removing device.

13. Method of using the polymerized composition according to claim 1 as a dental material, in particular as a fissure sealant, dental composite material, direct adhesive dental restoration, hoof repair material, bone cement, or bone cement for cementing artificial joint prostheses.

14. Method of using a polymerizable composition according to claim 1 in additive manufacturing processes, in radiation-based generative manufacturing processes, in a stereolithography process, SLA process (laser-based stereolithography process), a DLP process (digital light processing) or an SLA and DLP process, in LED beamer-based generative based manufacturing processes, in radiation- and thermally based generative manufacturing processes, in thermal generative manufacturing processes, in 3D printing processes, multitjet processes (MJM) or polyjet processes, in radiation and thermal based polymerization processes, in particular UV and/or VIS polymerization processes, free-radical induced polymerization processes, thermally based polymerization processes and/or redox-based polymerization processes.

15. Method according to claim 14 for the manufacture of dental prosthetic restorations comprising crowns, inlays, onlays, superstructures, artificial teeth, dental bridges, dental bars, spacers, abutments, veneers, or for manufacture a bite splint, milling blanks, dental prosthesis, part of a surgical prosthesis, drill guide, implant, mouthguard, joint prosthesis, telescope, implant part, orthodontic appliance, instrument or hoof part.

16. Polymerized composition according to claim 11, wherein $R^{10}$ each having independently a C1-C3 alkyl group or (meth)acryloxymethylene group.

* * * * *